(12) United States Patent
Aissaoui et al.

(10) Patent No.: US 8,697,869 B2
(45) Date of Patent: Apr. 15, 2014

(54) 3-(HETEROARYL-AMINO)-1,2,3,4-TETRAHYDRO-9H-CARBAZOLE DERIVATIVES AND THEIR USE AS PROSTAGLANDIN D2 RECEPTOR MODULATORS

(75) Inventors: Hamed Aissaoui, Pulversheim (FR); Heinz Fretz, Riehen (CH); Julien Hazemann, Sierentz (FR); Sylvia Richard-Bildstein, Dietwiller (FR); Romain Siegrist, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

(21) Appl. No.: 13/637,005

(22) PCT Filed: Mar. 21, 2011

(86) PCT No.: PCT/IB2011/051165
§ 371 (c)(1),
(2), (4) Date: Nov. 29, 2012

(87) PCT Pub. No.: WO2011/117798
PCT Pub. Date: Sep. 29, 2011

(65) Prior Publication Data
US 2013/0065902 A1    Mar. 14, 2013

(30) Foreign Application Priority Data

Mar. 22, 2010  (WO) .................. PCT/IB2010/051228

(51) Int. Cl.
C07D 239/02 (2006.01)
A61K 31/50 (2006.01)
(52) U.S. Cl.
USPC ..................................... 544/294; 514/252.06
(58) Field of Classification Search
USPC ..................................... 544/294; 514/252.06
See application file for complete search history.

(56) References Cited

U.S. PATENT DOCUMENTS

| 4,808,608 | A | 2/1989 | Guindon et al. |
| 4,965,258 | A | 10/1990 | Boshagen et al. |
| 2005/0171143 | A1 | 8/2005 | Tanimoto et al. |
| 2007/0191416 | A1 | 8/2007 | Fecher et al. |
| 2007/0208004 | A1 | 9/2007 | Fecher et al. |
| 2009/0270414 | A1 | 10/2009 | Fecher et al. |
| 2010/0063103 | A1 | 3/2010 | Armer et al. |
| 2010/0190830 | A1 | 7/2010 | Fretz et al. |
| 2010/0234396 | A1 | 9/2010 | Fecher et al. |
| 2011/0311483 | A1 | 12/2011 | Jia et al. |

FOREIGN PATENT DOCUMENTS

| EP | 0242518 | 4/1991 |
| EP | 1505061 | 2/2005 |
| EP | 1600400 | 11/2005 |
| EP | 1852420 | 11/2007 |
| EP | 1911759 | 4/2008 |
| EP | 1916245 | 4/2008 |
| EP | 1932839 | 6/2008 |
| GB | 2388540 | 11/2003 |
| GB | 2407318 | 4/2005 |
| GB | 2422829 | 8/2006 |
| GB | 2422830 | 8/2006 |
| GB | 2422831 | 8/2006 |
| WO | WO 01/78697 | 10/2001 |
| WO | WO 01/79169 | 10/2001 |
| WO | WO 02/094830 | 11/2002 |
| WO | WO 03/051837 | 6/2003 |
| WO | WO 03/062200 | 7/2003 |
| WO | WO 03/066046 | 8/2003 |
| WO | WO 03/066047 | 8/2003 |
| WO | WO 03/097042 | 11/2003 |
| WO | WO 03/101961 | 12/2003 |
| WO | WO 03/101981 | 12/2003 |
| WO | WO 2004/007451 | 1/2004 |
| WO | WO 2004/039807 | 5/2004 |
| WO | WO 2004/078719 | 9/2004 |
| WO | WO 2004/103970 | 12/2004 |
| WO | WO 2004/106302 | 12/2004 |
| WO | WO 2004/111047 | 12/2004 |
| WO | WO 2005/019171 | 3/2005 |
| WO | WO 2005/033099 | 4/2005 |

(Continued)

OTHER PUBLICATIONS

Arimura A. et al., "Prevention of Allergic Inflammation by a Novel Prostaglandin Receptor Antagonist, S-5751," J Pharmacol Exp Ther Aug. 1, 2001, 298, pp. 411-419.
Birkinshaw, Timothy N. et al., "Discovery of Potent CRTh2 ($DP_2$) Receptor Antagonists" Bioorg. Med. Chem Let. (2006), 16, pp. 4287-4290.
Fortini A et al., "Heparin Does Not Interfere with Prostacyclin and prostaglandin $D_2$ Binding to Platelets" (1985) Thromb Res 40 (3), pp. 319-328.
Gould, Philip, "Salt selection for basic drugs," International Journal of Pharmaceuticals, (1986) 33, pp. 201-217.
Greene, Theodora, P.G.M. Wuts, Protecting Groups in Organic Synthesis, Wiley-Interscience, 1999.

(Continued)

Primary Examiner — Robert Havlin
(74) Attorney, Agent, or Firm — Hunton & Williams LLP

(57) ABSTRACT

The present invention relates to 3-(heteroaryl-amino)-1,2,3,4-tetrahydro-9H-carbazole derivatives of the formula (I),

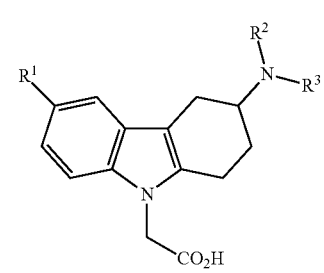

(I)

wherein $R^1$, $R^2$ and $R^3$ are as described in the description and their use as prostaglandin receptor modulators, most particularly as prostaglandin $D_2$ receptor modulators, in the treatment of various prostaglandin-mediated diseases and disorders, to pharmaceutical compositions containing these compounds and to processes for their preparation.

25 Claims, No Drawings

(56) References Cited

FOREIGN PATENT DOCUMENTS

| | | |
|---|---|---|
| WO | WO 2005/040112 | 5/2005 |
| WO | WO 2005/040114 | 5/2005 |
| WO | WO 2005/044260 | 5/2005 |
| WO | WO 2005/054232 | 6/2005 |
| WO | WO 2005/056527 | 6/2005 |
| WO | WO 2005/073234 | 8/2005 |
| WO | WO 2005/121141 | 12/2005 |
| WO | WO 2005/123731 | 12/2005 |
| WO | WO 2006/034418 | 3/2006 |
| WO | WO 2006/034419 | 3/2006 |
| WO | WO 2006/036994 | 4/2006 |
| WO | WO 2006/063763 | 6/2006 |
| WO | WO 2006/081343 | 8/2006 |
| WO | WO 2006/090817 | 8/2006 |
| WO | WO 2006/092579 | 9/2006 |
| WO | WO 2006095183 | 9/2006 |
| WO | WO 2006/125784 | 11/2006 |
| WO | WO 2006136859 | 12/2006 |
| WO | WO 2007/010964 | 1/2007 |
| WO | WO 2007/010965 | 1/2007 |
| WO | WO 2007/019675 | 2/2007 |
| WO | WO 2007/022501 | 2/2007 |
| WO | WO 2007/029629 | 3/2007 |
| WO | WO 2007/031747 | 3/2007 |
| WO | WO 2007/045867 | 3/2007 |
| WO | WO 2007/065683 | 6/2007 |
| WO | WO 2007/065684 | 6/2007 |
| WO | WO 2007/065924 | 6/2007 |
| WO | WO 2007/068418 | 6/2007 |
| WO | WO 2007/107772 | 9/2007 |
| WO | WO 2007/138282 | 12/2007 |
| WO | WO 2007/144127 | 12/2007 |
| WO | WO 2008/012511 | 1/2008 |
| WO | WO 2008/014186 | 1/2008 |
| WO | WO 2008/017989 | 2/2008 |
| WO | WO 2008/074966 | 6/2008 |
| WO | WO 2008/078069 | 7/2008 |
| WO | WO 2008/113965 | 9/2008 |
| WO | WO 2009/044134 | 4/2009 |
| WO | WO 2009/044147 | 4/2009 |
| WO | WO 2009/049021 | 4/2009 |
| WO | WO 2009/061676 | 5/2009 |
| WO | WO 2009/063202 | 5/2009 |
| WO | WO 2009/063215 | 5/2009 |
| WO | WO 2009/077728 | 6/2009 |
| WO | WO 2009/090399 | 7/2009 |
| WO | WO 2009/090414 | 7/2009 |
| WO | WO 2009/093026 | 7/2009 |
| WO | WO 2009/093029 | 7/2009 |
| WO | WO 2009/096526 | 8/2009 |
| WO | WO 2009/140642 | 11/2009 |
| WO | WO 2010/006939 | 1/2010 |
| WO | WO 2010/006944 | 1/2010 |
| WO | WO 2010/008864 | 1/2010 |
| WO | WO 2010/031182 | 3/2010 |
| WO | WO 2010/031183 | 3/2010 |
| WO | WO 2010/031184 | 3/2010 |
| WO | WO 2010/039982 | 4/2010 |
| WO | WO 2010/054113 | 5/2010 |
| WO | WO 2010/054114 | 5/2010 |
| WO | WO 2010/085820 | 7/2010 |
| WO | WO 2010/099039 | 9/2010 |
| WO | WO 2010/142934 | 12/2010 |
| WO | WO 2011/006936 | 1/2011 |
| WO | WO 2011/055270 | 5/2011 |
| WO | WO 2012/009134 | 7/2011 |
| WO | WO 2012/009137 | 1/2012 |
| WO | 2012/140612 | 10/2012 |

OTHER PUBLICATIONS

Ha, J. D et. al., "Synthesis of Tetrahydrocarbozole Derivatives as Potent β3-Andrenoceptor Agonists" (2004) Bulletin of the Korean Chemical Society 25 (12), pp. 1784-1790.

Ishizuka, T. et al., "Ramatroban (BAY u3405): A Novel Dual Antagonist of $TXA_2$ Receptor and CRTH2, a Newly Identified Prostagladin $D_2$ Receptor" Cardiovascular Drug Rev. 2004, 22(2), pp. 71-90.

Remington: The Science and Practice of Pharmacy, $21^{st}$ Edition, Lippincott, Williams and Wilkins Publishing, The University of the Sciences in Philadelphia, 2005.

Robarge, M. J. et al., "Isosteric Ramatroban Analogs: Selective and Potent CRTH-2 Antagonists" Bioorg. Med. Chem Let. (2005), 15, pp. 1749-1753.

Rosentreter U et al., "Synthesis and Absolute Configuration of the New Thromboxane Antagonist (3R)-3-(4-Fluorophenylsulfonamido)-1,2,3,4-tetrahydro-9-carbozolepropanoic Acid and Comparison with its Enantiomer" (1989) Arzneimittelforschung 39 (12), pp. 1519-1521.

Royer, J. F et al., "A Novel Antagonist of Prostaglandin $D_2$ Blocks the Locomotion of Eosinophils and Basophils" Europ. J. Clin. Investigation (2008), 38, pp. 663-671.

Sandham, David A. et al., "7-Azaindole-3-acetic Acid Derivatives: Potent and Selective CRTH2 Receptor Antagonist" Bioorg. Med. Chem Let. (2009), 19, pp. 4794-4798.

Sawyer, N. et al., "Molecular Pharmacology of the Human Prostaglandin $D_2$ Receptor, CRTH2" Br. J. Pharmacology, (2002) 137, pp. 1163-1172.

Shimizu, T. et al., "Specific Binding of Prostaglandin $D_2$ to Rat Brain Synaptic Membrane", J. Biol. Chem., (1982), 257, pp. 13570-13575.

Stearns, Brian A.et al., "Novel Tricyclic Antagonists of the Prostaglandin D2 Receptor DP2 with Efficacy in a Murine Model of Allergic Rhinitis" Bioorg. Med. Chem Let. (2009), 19, pp. 4647-4651.

Sugimoto, H. et al., "An Orally Bioavailable Small Molecule Antagonist of CRTH2, Ramatroban (BAY u3405), Inhibits Prostagladin $D_2$-Induced Eosinophie Migration in Vitro" J Pharmacol Exp Ther Apr. 1, 2003, pp. 305347-305352.

Tumey, L. Nathan et al., "3-Indolyl Sultams as Selective CRTh2 Antagonists" Bioorg. Med. Chem Let. (2010), 20, pp. 3287-3290.

Ulven T. et al., "Minor Structural Modifications Convert the Dual TP/CRTH2 Antagonist Ramatroban into a Highly Selective and Potent CRTH2 Antagonist", J. Med. Chem., (2005), 48 (4), pp. 897-900.

Ulven, T. et al., "Synthesis and in vitro Evaluation of a Selective Antagonist and the Corresponding Radioligand for the Prostaglandin $D_2$ Receptor CRTH2" Bioorg. Med. Chem Let. (2007), 17, pp. 5924-5927.

International Search Report of PCT/IB2011/051165, mailed May 24, 2011.

Sugimoto, H. et al., "An Orally Bioavailable Small Molecule Antagonist of CRTH2, Ramatroban (BAY u3405), Inhibits Prostagladin $D_2$-Induced Eosinophie Migration in Vitro" J Pharmacol Exp Ther Apr. 1, (2003) 305:347-352.

3-(HETEROARYL-AMINO)-1,2,3,4-TETRAHYDRO-9H-CARBAZOLE DERIVATIVES AND THEIR USE AS PROSTAGLANDIN D2 RECEPTOR MODULATORS

CROSS-REFERENCE TO RELATED APPLICATIONS

This application is the national phase application of PCT/IB2011/051165, filed Mar. 21, 2011, which claims the benefit of PCT/IB2010/051228, filed Mar. 22, 2010, the contents of each are hereby incorporated by reference in their entirety.

FIELD OF THE INVENTION

The present invention relates to 3-(heteroaryl-amino-1,2,3,4-tetrahydro-9H-carbazol-9-yl)-acetic acid derivatives of formula (I) and their use as prostaglandin receptor modulators, most particularly as prostaglandin $D_2$ receptor ("DP receptor") modulators, in the treatment of various prostaglandin-mediated diseases and disorders, to pharmaceutical compositions containing these compounds and to processes for their preparation. In particular, such derivatives may be used alone or in pharmaceutical compositions for the treatment of both, chronic and acute allergic/immune diseases/disorders such as asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, systemic mast cell disorders, anaphylactic shock, urticaria, eczema, ulcerative colitis, chronic obstructive pulmonary disease (COPD), inflammatory bowel disease and rheumatoid arthritis; eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinohilic endocarditis (Loeffler's endocarditis), eosinophilia-myalgia syndrome, eosinophilic fasciitis, eosinohilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia and DRESS syndrome (Drug Rash with Eosinophilia and Systemic Symptoms); and basophil-related diseases, comprising basophilic leukemia and basophilic leukocytosis.

BACKGROUND OF THE INVENTION

As a response to allergen exposure in allergic conditions, mast cells are activated and release mediators like histamine, thromboxane A2 (TxA2), cysteinyl leukotrienes (CysLTs) and prostaglandin $D_2$ ($PGD_2$). These mediators interact with their respective receptors and cause physiological effects such as increased vascular permeability, edema, pruritus, nasal and pulmonary congestion, bronchoconstriction, and mucus secretion. An increased vascular permeability for example, allows excessive infiltration of eosinophilic and basophilic leukocytes into the tissue and thus amplifies the allergic response.

Current treatments of allergic diseases comprise agents that can block or otherwise interrupt such interactions, e.g. anti-histamines (histamine H1 receptor antagonists), leukotriene receptor antagonists, beta-adrenergic receptor agonists, and corticosteroids. Generally, treatments with anti-histamines and leukotriene antagonists are limited in efficacy, and long-term usage of corticosteroids is often associated with unwanted side effects.

$PGD_2$ is an agonist known to act on two G-protein-coupled receptors, the $PGD_2$ receptor DP1 and the recently identified CRTH2 (chemoattractant receptor-homologous molecule expressed on Th2 cells) receptor (also referred to as "DP2 receptor").

Elevated $PGD_2$ levels are considered to cause inflammation as observed in allergic diseases such as allergic rhinitis, allergic asthma, allergic conjunctivitis, atopic dermatitis and the like. Therefore, blocking the interaction of $PGD_2$ with its receptors is considered a useful therapeutic strategy for the treatment of such diseases.

WO 01/79169 discloses (tetrahydrocarbazol-1-yl)acetic acid derivatives as $PGD_2$ receptor antagonists.

GB 2388540 discloses the use of ramatroban ((3R)-3-(4-fluorobenzene-sulfonamido)-1,2,3,4-tetrahydrocarbazole-9-propionic acid), a TxA2 receptor (also referred to as "TP receptor") antagonist with additional antagonistic activity on CRTH2, for the prophylaxis and treatment of allergic diseases, such as asthma, allergic rhinitis or allergic conjunctivitis. In T. Ishizuka et al., *Cardiovascular Drug Rev.* 2004, 22(2), 71-90 effects of ramatroban on late-phase inflammation are described. Furthermore, oral bioavailability of ramatroban and its ability to inhibit prostaglandin $D_2$-induced eosinophil migration in vitro has been reported (*Journal of Pharmacology and Experimental Therapeutics,* 305(1), p. 347-352 (2003)).

WO 03/097598 and WO 03/097042 disclose Ramatroban analogues with CRTH2 antagonistic activity. Ulven et al, *J. Med. Chem.* 2005, 48(4), 897-900 disclose further ramatroban analogues.

WO 08/017,989 discloses (3-amino-1,2,3,4-tetrahydro-9H-carbazol-9-yl)acetic acid derivatives with CRTH2 antagonistic activity.

DESCRIPTION OF THE INVENTION

1) The present invention relates to 3-(heteroaryl-amino)-1,2,3,4-tetrahydro-9H-carbazole derivatives of the formula (I),

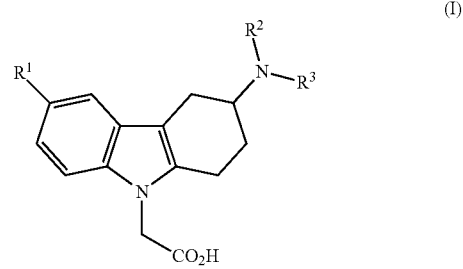

wherein
$R^1$ represents hydrogen, $(C_1-C_4)$alkyl, $(C_1-C_4)$alkoxy, halogen, trifluoromethoxy or trifluoromethyl;
$R^2$ represents hydrogen, $(C_1-C_4)$alkyl, $(C_1-C_2)$alkoxy-$(C_2-C_3)$alkyl, $(C_1-C_4)$fluoroalkyl or $(C_3-C_6)$cycloalkyl-$(C_1-C_2)$alkyl; and
$R^3$ represents a heteroaryl group which is unsubstituted or mono-, di- or tri-substituted, wherein the substituents are independently selected from the group consisting of halogen, $(C_1-C_4)$alkyl, $(C_3-C_6)$cycloalkyl, $(C_1-C_4)$alkoxy, $(C_1-C_4)$fluoroalkyl and phenyl;

and to the salts (in particular pharmaceutically acceptable salts) of such compounds.

The compounds of formula (I) according to embodiment 1) may contain one or more stereogenic or asymmetric centers, such as one or more asymmetric carbon atoms. Substituents at a double bond may be present in the (Z)- or (E)-configuration unless indicated otherwise. The compounds of formula (I) may thus be present as mixtures of stereoisomers or preferably as pure stereoisomers. Mixtures of stereoisomers may be separated in a manner known to a person skilled in the art.

The following paragraphs provide definitions of the various chemical moieties for the compounds according to the invention and are intended to apply uniformly throughout the specification and claims unless an otherwise expressly set out definition provides a broader or narrower definition.

The term "alkyl", used alone or in combination, refers to a straight or branched chain alkyl group containing one to four carbon atoms. The term "$(C_x-C_y)$alkyl" (x and y each being an integer), refers to an alkyl group as defined before containing x to y carbon atoms. For example a $(C_1-C_4)$alkyl group contains from one to four carbon atoms. Representative examples of alkyl groups include methyl, ethyl, n-propyl, iso-propyl, n-butyl, iso-butyl, sec-butyl and tert-butyl.

In case "$R^1$" represents "$(C_1-C_4)$alkyl" the term means $(C_1-C_4)$alkyl groups as defined above. Examples of said groups are methyl, ethyl, n-propyl, iso-propyl, n-butyl, iso-butyl, sec-butyl and tert-butyl. Preferred is methyl.

In case "$R^2$" represents "$(C_1-C_4)$alkyl" the term means $(C_1-C_4)$alkyl groups as defined above. Examples of said groups are methyl, ethyl, n-propyl, iso-propyl, n-butyl, iso-butyl, sec-butyl and tert-butyl. Preferred are methyl, ethyl and n-propyl; most preferred is methyl. In case "$R^3$" represents "heteroaryl which is substituted with $(C_1-C_4)$alkyl" the term "$(C_1-C_4)$alkyl" means $(C_1-C_4)$alkyl groups as defined above. Examples of said groups are methyl, ethyl, n-propyl, iso-propyl, n-butyl, iso-butyl, sec-butyl and tert-butyl. Preferred is methyl.

The term "alkoxy", used alone or in combination, refers to an alkyl-O— group wherein the alkyl group is as defined before. The term "$(C_x-C_y)$alkoxy" (x and y each being an integer) refers to an alkoxy group as defined before containing x to y carbon atoms. For example a $(C_1-C_4)$alkoxy group contains from one to four carbon atoms. Representative examples of alkoxy groups include methoxy, ethoxy, n-propoxy, iso-propoxy, n-butoxy, iso-butoxy, sec-butoxy and tert-butoxy.

In case "$R^1$" represents "$(C_1-C_4)$alkoxy" the term means $(C_1-C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

In case "$R^3$" represents "heteroaryl which is substituted with $(C_1-C_4)$alkoxy" the term "$(C_1-C_4)$alkoxy" means $(C_1-C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

The term "$(C_1-C_2)$alkoxy-$(C_2-C_3)$alkyl" refers to an $(C_2-C_3)$alkyl group as defined above in which one hydrogen atom has been replaced with an $(C_1-C_2)$alkoxy group as defined above. Examples of $(C_1-C_2)$alkoxy-$(C_2-C_3)$alkyl groups are methoxy-ethyl (notably 2-methoxy-ethyl), methoxy-propyl (notably 2-methoxy-propyl and 3-methoxy-propyl), ethoxy-ethyl (notably 2-ethoxy-ethyl) and ethoxy-propyl (notably 2-ethoxy-propyl and 3-ethoxy-propyl). Preferred is 2-methoxy-ethyl.

The term "$(C_3-C_6)$cycloalkyl", used alone or in combination, means a cycloalkyl group with 3 to 6 carbon atoms.

Examples of $(C_3-C_6)$cycloalkyl groups are cyclopropyl, cyclobutyl, cyclopentyl and cyclohexyl. Preferred is cyclopropyl.

The term "$(C_3-C_6)$cycloalkyl-$(C_1-C_2)$-alkyl" refers to an $(C_1-C_2)$alkyl group as defined above in which one hydrogen atom has been replaced with an $(C_3-C_6)$cycloalkyl group as defined above. Examples of $(C_3-C_6)$cycloalkyl-$(C_1-C_2)$alkyl groups are cyclopropyl-methyl, cyclobutyl-methyl, cyclopentyl-methyl, cyclohexyl-methyl, cyclopropyl-ethyl (notably 1-cyclopropyl-ethyl and 2-cyclopropyl-ethyl), cyclobutyl-ethyl (notably 1-cyclobutyl-ethyl and 2-cyclobutyl-ethyl), cyclopentyl-ethyl (notably 1-cyclopentyl-ethyl and 2-cyclopentyl-ethyl) and cyclohexyl-ethyl (notably 1-cyclohexyl-ethyl and 2-cyclohexyl-ethyl). Preferred is cyclopropyl-methyl.

The term "$(C_x-C_y)$fluoroalkyl" (x and y each being an integer) refers to an alkyl group as defined before containing x to y carbon atoms in which one or more (and possibly all) hydrogen atoms have been replaced with fluorine. For example a $(C_1-C_4)$fluoroalkyl group contains from one to four carbon atoms in which one to nine hydrogen atoms have been replaced with fluorine.

In case "$R^2$" represents "$(C_1-C_4)$fluoroalkyl" the term means a $(C_1-C_4)$fluoroalkyl group as defined above. Examples of said groups are difluoromethyl, trifluoromethyl, 2,2-difluoroethyl and 2,2,2-trifluoroethyl. Preferred examples are 2,2-difluoroethyl and 2,2,2-trifluoroethyl. Most preferred is 2,2-difluoroethyl.

In case "$R^3$" represents "heteroaryl which is substituted with $(C_1-C_4)$fluoroalkyl" the term "$(C_1-C_4)$fluoroalkyl" means a $(C_1-C_4)$fluoroalkyl group as defined above. Examples of said groups are difluoromethyl, trifluoromethyl, 2,2-difluoroethyl and 2,2,2-trifluoroethyl. Preferred examples are difluoromethyl and trifluoromethyl. Most preferred is trifluoromethyl.

The term halogen means fluoro, chloro, bromo or iodo.

In case "$R^1$" represents "halogen" the term means preferably fluorine and chlorine and most preferably fluorine.

In case "$R^3$" represents "heteroaryl which is substituted with halogen" the term "halogen" means preferably fluorine, chlorine and bromine, more preferably fluorine and chlorine and most preferably chlorine.

The term "heteroaryl", used alone or in combination, means a 5- to 10-membered monocyclic or bicyclic aromatic ring containing 1, 2 or 3 heteroatoms independently selected from oxygen, nitrogen and sulfur. Preferably the term "heteroaryl" means a 5- to 10-membered monocyclic or bicyclic aromatic ring containing one nitrogen atom and optionally one additional heteroatom selected from oxygen, nitrogen and sulfur. Most preferred are 6-membered monocyclic aromatic ring systems containing one or two nitrogen atoms. Examples of such heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzo[2,1,3]oxadiazolyl, benzo[2,1,3]thiadiazolyl, benzo[1,2,3]thiadiazolyl, quinolinyl, isoquinolinyl, cinnolinyl, quinazolinyl, quinoxalinyl and phthalazinyl. Preferred examples of such heteroaryl groups are pyridyl (notably pyridin-2-yl), pyrimidyl (notably pyrimidin-2-yl), benzoxazolyl (notably benzoxazol-2-yl), benzothiazolyl (notably benzothiazol-2-yl) and quinazolinyl (notably quinazolin-2-yl and quinazolin-4-yl). Further preferred examples are isoxazolyl (notably isoxazol-3-yl), thiazolyl (notably thiazol-2-yl), thiadiazolyl (notably thiadiazol- 2-yl), pyrazolyl (notably pyrazol-3-yl) and quinoxalinyl (notably quinoxalin-2-yl). More preferred are pyrimidyl (notably pyrimidin-2-yl), benzoxazolyl (notably benzoxazol-2-yl) and benzothiazolyl (notably benzothiazol-2-yl). Most preferred is pyrimidyl (notably pyrimidin-2-yl). The heteroaryl group may be unsubstituted or mono-, di- or tri-substituted (preferably unsubstituted or mono-substituted and most preferably mono-substituted), wherein the substituents are independently selected from the group consisting of halogen, $(C_1-C_4)$alkyl, $(C_3-C_6)$cycloalkyl, $(C_1-C_4)$alkoxy, $(C_1-C_4)$fluoroalkyl and phenyl (and notably halogen, $(C_1-C_4)$alkyl, $(C_1-C_4)$alkoxy, $(C_1-C_4)$fluoroalkyl and phenyl). Examples of such unsubstituted, mono-, di- or tri-substituted heteroaryl groups are 5-fluoro-pyridin-2-yl, 5-chloro-pyridin-2-yl, 5-trifluoromethyl-pyridin-2-yl, pyrimidin-2-yl, 5-fluoro-pyrimidin-2-yl, 5-chloro-pyrimidin-2-yl, 4-methyl-pyrimidin-2-yl, 4,6-dimethyl-pyrimidin-2-yl, 5-methoxy-pyrimidin-2-yl, 4-trifluoromethyl-pyrimidin-2-yl, 5-trifluoromethyl-pyrimidin-2-yl, 5-phenyl-pyrimidin-2-yl, benzoxazol-2-yl, 5-fluoro-benzoxazol-2-yl, 5-chloro-benzoxazol-2-yl, 6-chloro-benzoxazol-2-yl, benzothiazol-2-yl, 5-fluoro-benzothiazol-2-yl, 6-fluoro-benzothiazol-2-yl, 5-chloro-benzothiazol-2-yl, 6-chloro-benzothiazol-2-yl, quinazolin-2-yl, quinazolin-4-yl, 2-methyl-quinazolin-4-yl and 2-trifluoromethyl-quinazolin-4-yl. Further examples are isoxazol-3-yl, 5-methyl-isoxazol-3-yl, 5-tert-butyl-isoxazol-3-yl, 4-methyl-thiazol-2-yl, 4-tert-butyl-thiazol-2-yl, 4-trifluoromethyl-thiazol-2-yl, 5-methyl-thiadiazol-2-yl, 1-methyl-pyrazol-3-yl, 5-cyclopropyl-pyrimidin-2-yl, 6-fluoro-benzoxazol-2-yl and quinoxalin-2-yl. Preferred examples are 5-fluoro-pyridin-2-yl, 5-chloro-pyridin-2-yl, 5-fluoro-pyrimidin-2-yl, 5-chloro-pyrimidin-2-yl, 5-trifluoromethyl-pyrimidin-2-yl, 5-fluoro-benzoxazol-2-yl, 5-chloro-benzoxazol-2-yl, 5-chloro-benzothiazol-2-yl and 6-chloro-benzothiazol-2-yl. Further preferred examples are 6-fluoro-benzoxazol-2-yl, 5-fluoro-benzothiazol-2-yl and 6-fluoro-benzothiazol-2-yl. Most preferred is 5-chloro-pyrimidin-2-yl.

2) A further embodiment of the invention relates to compounds according to embodiment 1), wherein
$R^1$ represents hydrogen, $(C_1-C_4)$alkyl, $(C_1-C_4)$alkoxy, halogen, trifluoromethoxy or trifluoromethyl;
$R^2$ represents hydrogen, $(C_1-C_4)$alkyl, $(C_1-C_2)$alkoxy-$(C_2-C_3)$alkyl, $(C_1-C_4)$fluoroalkyl or $(C_3-C_6)$cycloalkyl-$(C_1-C_2)$alkyl; and
$R^3$ represents a heteroaryl group which is unsubstituted or mono-, di- or tri-substituted, wherein the substituents are independently selected from the group consisting of halogen, $(C_1-C_4)$alkyl, $(C_1-C_4)$alkoxy, $(C_1-C_4)$fluoroalkyl and phenyl;
and to the salts (in particular pharmaceutically acceptable salts) of such compounds.

3) A further embodiment of the invention relates to compounds according to embodiment 1), wherein
$R^1$ represents hydrogen, methyl, methoxy, halogen (notably fluorine or chlorine) or trifluoromethyl;
$R^2$ represents hydrogen, $(C_1-C_4)$alkyl, $(C_1-C_2)$alkoxy-$(C_2-C_3)$alkyl, $(C_1-C_4)$fluoroalkyl or $(C_3-C_6)$cycloalkyl-$(C_1-C_2)$alkyl; and
$R^3$ represents a heteroaryl group which is unsubstituted or mono- or di-substituted (notably unsubstituted or mono-substituted), wherein the substituents are independently selected from the group consisting of halogen, $(C_1-C_4)$alkyl, $(C_3-C_6)$cycloalkyl, $(C_1-C_4)$alkoxy, $C_4)$fluoroalkyl and phenyl;
and to the salts (in particular pharmaceutically acceptable salts) of such compounds.

4) A further embodiment of the invention relates to compounds according to any one of embodiments 1) or 2), wherein
$R^1$ represents hydrogen, halogen (notably fluorine) or trifluoromethyl;
$R^2$ represents hydrogen, $(C_1-C_4)$alkyl, $(C_1-C_2)$alkoxy-$(C_2-C_3)$alkyl, $(C_1-C_4)$fluoroalkyl or $(C_3-C_6)$cycloalkyl-$(C_1-C_2)$alkyl; and
$R^3$ represents a heteroaryl group which is unsubstituted or mono- or di-substituted, wherein the substituents are independently selected from the group consisting of halogen, $(C_1-C_4)$alkyl, $(C_1-C_4)$alkoxy, $(C_1-C_4)$fluoroalkyl and phenyl;
and to the salts (in particular pharmaceutically acceptable salts) of such compounds.

5) A further embodiment of the invention relates to compounds according to any one of embodiments 1) to 4), wherein
$R^1$ represents halogen (notably fluorine);
$R^2$ represents hydrogen, methyl, ethyl, n-propyl, 2-methoxy-ethyl, 2,2-difluoroethyl or cyclopropyl-methyl; and
$R^3$ represents a heteroaryl group which is unsubstituted or mono-substituted with halogen (notably fluorine or chlorine), methoxy, trifluoromethyl or phenyl;
and to the salts (in particular pharmaceutically acceptable salts) of such compounds.

6) A further embodiment of the invention relates to compounds according to any one of embodiments 1) to 4), wherein
$R^1$ represents fluorine, chlorine or trifluoromethyl;
$R^2$ represents hydrogen, methyl, 2-methoxy-ethyl or cyclopropyl-methyl; and
$R^3$ represents a heteroaryl group which is mono-substituted with fluorine or chlorine;
and to the salts (in particular pharmaceutically acceptable salts) of such compounds.

7) A further embodiment of the invention relates to compounds according to any one of embodiments 1) to 6), wherein
$R^1$ represents fluorine;
$R^2$ represents methyl or 2-methoxy-ethyl; and
$R^3$ represents a heteroaryl group which is mono-substituted with fluorine or chlorine; and to the salts (in particular pharmaceutically acceptable salts) of such compounds.

8) A further embodiment of the invention relates to compounds according to any one of embodiments 1) to 6), wherein
$R^1$ represents fluorine;
$R^2$ represents hydrogen or methyl; and
$R^3$ represents a heteroaryl group which is unsubstituted or mono-substituted with fluorine, chlorine or trifluoromethyl (notably fluorine or chlorine);
and to the salts (in particular pharmaceutically acceptable salts) of such compounds.

9) A further embodiment of the invention relates to compounds according to any one of embodiments 1) to 4), wherein
$R^1$ represents hydrogen, halogen (notably fluorine) or trifluoromethyl;
and to the salts (in particular pharmaceutically acceptable salts) of such compounds.

10) A further embodiment of the invention relates to compounds according to any one of embodiments 1) to 6), wherein
$R^1$ represents halogen (notably fluorine);
and to the salts (in particular pharmaceutically acceptable salts) of such compounds.

11) A further embodiment of the invention relates to compounds according to any one of embodiments 1) to 4), 9) or 10), wherein $R^2$ represents hydrogen, $(C_1-C_4)$alkyl, $(C_1-C_2)$alkoxy-$(C_2-C_3)$alkyl or $(C_3-C_6)$cycloalkyl-$(C_1-C_2)$alkyl;
and to the salts (in particular pharmaceutically acceptable salts) of such compounds.

12) A further embodiment of the invention relates to compounds according to any one of embodiments 1) to 5) or 9) to 10), wherein
$R^2$ represents hydrogen, methyl, ethyl, n-propyl, 2-methoxyethyl, 2,2-difluoroethyl or cyclopropyl-methyl;
and to the salts (in particular pharmaceutically acceptable salts) of such compounds.

13) A further embodiment of the invention relates to compounds according to any one of embodiments 1) to 6) or 8) to 10), wherein
$R^2$ represents hydrogen or methyl;
and to the salts (in particular pharmaceutically acceptable salts) of such compounds.

14) A further embodiment of the invention relates to compounds according to any one of embodiments 1) to 10), wherein
$R^2$ represents $(C_1-C_4)$alkyl (notably methyl);
and to the salts (in particular pharmaceutically acceptable salts) of such compounds.

15) A further embodiment of the invention relates to compounds according to any one of embodiments 1) to 4) or 9) to 14), wherein
$R^3$ represents a heteroaryl group which is unsubstituted or mono- or di-substituted, wherein the substituents are independently selected from the group consisting of halogen, $(C_1-C_4)$alkyl, $(C_1-C_4)$alkoxy, $(C_1-C_4)$fluoroalkyl and phenyl;
and to the salts (in particular pharmaceutically acceptable salts) of such compounds.

16) A further embodiment of the invention relates to compounds according to any one of embodiments 1) to 5) or 9) to 14), wherein
$R^3$ represents a heteroaryl group which is unsubstituted or mono-substituted with halogen (notably fluorine or chlorine), methoxy, trifluoromethyl or phenyl;
and to the salts (in particular pharmaceutically acceptable salts) of such compounds.

17) A further embodiment of the invention relates to compounds according to any one of embodiments 1), 3), or 9) to 14), wherein
$R^3$ represents a heteroaryl group which is unsubstituted or mono-substituted with halogen, $(C_3-C_6)$cycloalkyl or $(C_1-C_4)$fluoroalkyl (and notably fluorine, chlorine, cyclopropyl or trifluoromethyl);
and to the salts (in particular pharmaceutically acceptable salts) of such compounds.

18) A further embodiment of the invention relates to compounds according to any one of embodiments 1) to 5) or 8) to 14), wherein
$R^3$ represents a heteroaryl group which is unsubstituted or mono-substituted with fluorine, chlorine or trifluoromethyl;
and to the salts (in particular pharmaceutically acceptable salts) of such compounds.

19) A further embodiment of the invention relates to compounds according to any one of embodiments 1) to 14), wherein
$R^3$ represents a heteroaryl group which is unsubstituted or mono-substituted with fluorine, chlorine or trifluoromethyl (notably mono-substituted with fluorine or chlorine), wherein the heteroaryl is selected from the group consisting of pyrimidyl (notably pyrimidin-2-yl), benzoxazolyl (notably benzoxazol-2-yl) and benzothiazolyl (notably benzothiazol-2-yl);
and to the salts (in particular pharmaceutically acceptable salts) of such compounds.

20) A further embodiment of the invention relates to compounds according to any one of embodiments 1) to 5) or 8) to 14), wherein
$R^3$ represents pyrimidin-2-yl which is unsubstituted or mono-substituted with halogen, methoxy, trifluoromethyl or phenyl (and notably unsubstituted or mono-substituted in the 5-position with fluorine, chlorine or trifluoromethyl);
and to the salts (in particular pharmaceutically acceptable salts) of such compounds.

21) A further embodiment of the invention relates to compounds according to any one of embodiments 1) to 14), wherein
$R^3$ represents 5-chloro-pyrimidin-2-yl;
and to the salts (in particular pharmaceutically acceptable salts) of such compounds.

22) A further embodiment of the invention relates to compounds according to any one of embodiments 1) to 14), wherein
$R^3$ represents a benzoxazol-2-yl- or a benzothiazol-2-yl-group, which groups are optionally mono-substituted with fluorine or chlorine;
and to the salts (in particular pharmaceutically acceptable salts) of such compounds.

23) A further embodiment of the invention relates to compounds according to any one of embodiments 1) to 22), wherein the absolute configuration of the stereogenic center is as depicted in formula $I_{St1}$

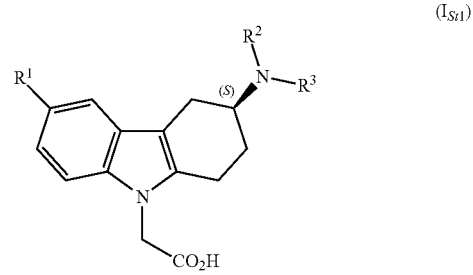

($I_{St1}$)

and to the salts (in particular pharmaceutically acceptable salts) of such compounds.

24) A further embodiment of the invention relates to compounds according to any one of embodiments 1) to 22), wherein the absolute configuration of the stereogenic center is as depicted in formula $I_{St2}$

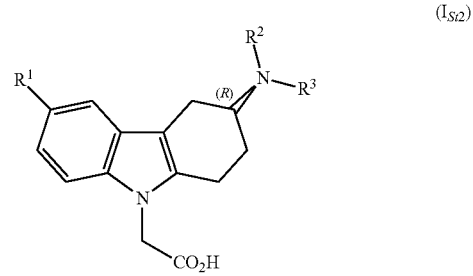

($I_{St2}$)

and to the salts (in particular pharmaceutically acceptable salts) of such compounds.

25) A further embodiment of the invention relates to compounds according to embodiment 1), which are also compounds of formula $I_{St1}$

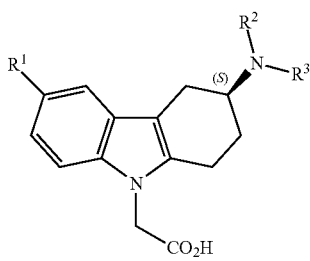

wherein
R¹ represents fluorine or chlorine (notably fluorine);
R² represents hydrogen or methyl (notably methyl); and
R³ represents pyrimidin-2-yl which is mono-substituted in 5-position with fluorine or chlorine; benzoxazol-2-yl which is mono-substituted in 5- or 6-position with fluorine; or benzothiazol-2-yl which is mono-substituted in 5- or 6-position with fluorine;
and to the salts (in particular pharmaceutically acceptable salts) of such compounds.

26) Preferred compounds of formula (I) as defined in embodiment 1) are selected from the group consisting of:
(3S)-2-(6-fluoro-3-((5-fluoropyrimidin-2-yl)amino)-3,4-dihydro-1H-carbazol-9-(2H)-yl)acetic acid;
(3R)-2-(6-fluoro-3-((5-fluoropyrimidin-2-yl)amino)-3,4-dihydro-1H-carbazol-9-(2H)-yl)acetic acid;
(3S)-2-(6-fluoro-3-((5-chloropyrimidin-2-yl)amino)-3,4-dihydro-1H-carbazol-9-(2H)-yl)acetic acid;
(3R)-2-(6-fluoro-3-((5-chloropyrimidin-2-yl)amino)-3,4-dihydro-1H-carbazol-9-(2H)-yl)acetic acid;
(3R)-2-(6-fluoro-3-((5-(trifluoromethyl)pyrimidin-2-yl)amino)-3,4-dihydro-1H-carbazol-9-(2H)-yl)acetic acid;
(3R)-2-(6-fluoro-3-((4-(trifluoromethyl)pyrimidin-2-yl)amino)-3,4-dihydro-1H-carbazol-9-(2H)-yl)acetic acid;
(3S)-2-(6-fluoro-3-((5-fluoropyrimidin-2-yl)(methyl)amino)-3,4-dihydro-1H-carbazol-9(2H)-yl)acetic acid;
(3R)-2-(6-fluoro-3-((5-fluoropyrimidin-2-yl)(methyl)amino)-3,4-dihydro-1H-carbazol-9(2H)-yl)acetic acid;
(3S)-2-(3-((5-chloropyrimidin-2-yl)(methyl)amino)-6-fluoro-3,4-dihydro-1H-carbazol-9(2H)-yl)acetic acid;
(3R)-2-(3-((5-chloropyrimidin-2-yl)(methyl)amino)-6-fluoro-3,4-dihydro-1H-carbazol-9(2H)-yl)acetic acid;
(3S)-2-(6-fluoro-3-(methyl(5-(trifluoromethyl)pyrimidin-2-yl)amino)-3,4-dihydro-1H-carbazol-9(2H)-yl)acetic acid;
(3R)-2-(6-fluoro-3-(methyl(5-(trifluoromethyl)pyrimidin-2-yl)amino)-3,4-dihydro-1H-carbazol-9(2H)-yl)acetic acid;
(3S)-2-(6-fluoro-3-(methyl(4-(trifluoromethyl)pyrimidin-2-yl)amino)-3,4-dihydro-1H-carbazol-9(2H)-yl)acetic acid;
(3R)-2-(6-fluoro-3-(methyl(4-(trifluoromethyl)pyrimidin-2-yl)amino)-3,4-dihydro-1H-carbazol-9(2H)-yl)acetic acid;
(3S)-2-(6-fluoro-3-(methyl(pyrimidin-2-yl)amino)-3,4-dihydro-1H-carbazol-9(2H)-yl)acetic acid;
(3S)-2-(3-((4,6-dimethylpyrimidin-2-yl)(methyl)amino)-6-fluoro-3,4-dihydro-1H-carbazol-9(2H)-yl)acetic acid;
(3S)-2-(6-fluoro-3-(methyl(4-methylpyrimidin-2-yl)amino)-3,4-dihydro-1H-carbazol-9(2H)-yl)acetic acid;
(3S)-2-(3-((5-chlorobenzo[d]oxazol-2-yl)(methyl)amino)-6-fluoro-3,4-dihydro-1H-carbazol-9(2H)-yl)acetic acid;
(3S)-2-(3-(benzo[d]oxazol-2-yl(methyl)amino)-6-fluoro-3,4-dihydro-1H-carbazol-9(2H)-yl)acetic acid;
(3S)-2-(3-(benzo[d]thiazol-2-yl(methyl)amino)-6-fluoro-3,4-dihydro-1H-carbazol-9(2H)-yl)acetic acid;
(3S)-2-(6-fluoro-3-(methyl(quinazolin-4-yl)amino)-3,4-dihydro-1H-carbazol-9(2H)-yl)acetic acid;
(3S)-2-(6-fluoro-3-(methyl(2-(trifluoromethyl)quinazolin-4-yl)amino)-3,4-dihydro-1H-carbazol-9(2H)-yl)acetic acid;
(3S)-2-(6-fluoro-3-(methyl(2-methylquinazolin-4-yl)amino)-3,4-dihydro-1H-carbazol-9(2H)-yl)acetic acid;
(3S)-2-(3-((5-chloropyrimidin-2-yl)(ethyl)amino)-6-fluoro-3,4-dihydro-1H-carbazol-9(2H)-yl)acetic acid;
(3S)-2-(3-((5-chloropyrimidin-2-yl)(propyl)amino)-6-fluoro-3,4-dihydro-1H-carbazol-9(2H)-yl)acetic acid;
(3S)-2-(3-((5-chloropyrimidin-2-yl)(isopropyl)amino)-6-fluoro-3,4-dihydro-1H-carbazol-9(2H)-yl)acetic acid;
(3S)-2-(3-((5-chloropyrimidin-2-yl)(cyclopropylmethyl)amino)-6-fluoro-3,4-dihydro-1H-carbazol-9(2H)-yl) acetic acid;
(3S)-2-(6-fluoro-3-(methyl(quinazolin-2-yl)amino)-3,4-dihydro-1H-carbazol-9(2H)-yl)acetic acid;
(3S)-2-(6-fluoro-3-((5-fluorobenzo[d]oxazol-2-yl)(methyl)amino)-3,4-dihydro-1H-carbazol-9(2H)-yl)acetic acid;
(3S)-2-(6-fluoro-3-(methyl(5-phenylpyrimidin-2-yl)amino)-3,4-dihydro-1H-carbazol-9(2H)-yl)acetic acid;
(3S)-2-(6-fluoro-3-((5-methoxypyrimidin-2-yl)(methyl)amino)-3,4-dihydro-1H-carbazol-9(2H)-yl)acetic acid;
(3S)-2-(3-((6-chlorobenzo[d]thiazol-2-yl)(methyl)amino)-6-fluoro-3,4-dihydro-1H-carbazol-9(2H)-yl)acetic acid;
(3S)-2-(3-((5-chlorobenzo[d]thiazol-2-yl)(methyl)amino)-6-fluoro-3,4-dihydro-1H-carbazol-9(2H)-yl)acetic acid;
(3S)-2-(3-((5-chloropyrimidin-2-yl)(2-methoxyethyl)amino)-6-fluoro-3,4-dihydro-1H-carbazol-9(2H)-yl)acetic acid;
(3S)-2-(6-fluoro-3-(methyl(5-(trifluoromethyl)pyridin-2-yl)amino)-3,4-dihydro-1H-carbazol-9(2H)-yl)acetic acid;
(3S)-2-(6-fluoro-3-((5-fluoropyridin-2-yl)(methyl)amino)-3,4-dihydro-1H-carbazol-9(2H)-yl)acetic acid;
(3S)-2-(3-((5-chloropyridin-2-yl)(methyl)amino)-6-fluoro-3,4-dihydro-1H-carbazol-9(2H)-yl)acetic acid;
(3S)-2-(6-fluoro-3-((6-fluorobenzo[d]thiazol-2-yl)(methyl)amino)-3,4-dihydro-1H-carbazol-9(2H)-yl)acetic acid;
(3S)-2-(6-fluoro-3-((5-fluorobenzo[d]thiazol-2-yl)(methyl)amino)-3,4-dihydro-1H-carbazol-9(2H)-yl)acetic acid;
(3S)-2-(6-fluoro-3-((6-chlorobenzo[d]oxazol-2-yl)(methyl)amino)-3,4-dihydro-1H-carbazol-9(2H)-yl)acetic acid; and
(3S)-2-(3-((5-chloropyrimidin-2-yl)(2,2-difluoroethyl)amino)-6-fluoro-3,4-dihydro-1H-carbazol-9(2H)-yl) acetic acid;
or salts (in particular pharmaceutically acceptable salts) of such compounds.

27) Further preferred compounds of formula (I) as defined in embodiment 1) are selected from the group consisting of:
(3S)-2-(3-((5-cyclopropylpyrimidin-2-yl)(methyl)amino)-6-fluoro-3,4-dihydro-1H-carbazol-9(2H)-yl)acetic acid;
(3S)-2-(6-fluoro-3-((6-fluorobenzo[d]oxazol-2-yl)(methyl)amino)-3,4-dihydro-1H-carbazol-9(2H)-yl)acetic acid;
(3S)-2-(6-fluoro-3-(methyl(quinoxalin-2-yl)amino)-3,4-dihydro-1H-carbazol-9(2H)-yl)acetic acid;
2-(6-fluoro-3-(methyl(4-methylthiazol-2-yl)amino)-3,4-dihydro-1H-carbazol-9(2H)-yl)acetic acid;
2-(3-((4-(tert-butyl)thiazol-2-yl)(methyl)amino)-6-fluoro-3,4-dihydro-1H-carbazol-9(2H)-yl)acetic acid;
2-(6-fluoro-3-(methyl(4-(trifluoromethyl)thiazol-2-yl)amino)-3,4-dihydro-1H-carbazol-9(2H)-yl)acetic acid;
2-(3-((5-(tert-butyl)isoxazol-3-yl)(methyl)amino)-6-fluoro-3,4-dihydro-1H-carbazol-9(2H)-yl)acetic acid;
2-(6-fluoro-3-(methyl(1-methyl-1H-pyrazol-3-yl)amino)-3,4-dihydro-1H-carbazol-9(2H)-yl)acetic acid;
2-(6-fluoro-3-(methyl(5-methyl-1,3,4-thiadiazol-2-yl)amino)-3,4-dihydro-1H-carbazol-9(2H)-yl)acetic acid;

2-(6-fluoro-3-(isoxazol-3-yl(methyl)amino)-3,4-dihydro-1H-carbazol-9(2H)-yl)acetic acid;
2-(6-fluoro-3-(methyl(5-methylisoxazol-3-yl)amino)-3,4-dihydro-1H-carbazol-9(2H)-yl)acetic acid;
2-(3-((5-chloropyrimidin-2-yl)(methyl)amino)-3,4-dihydro-1H-carbazol-9(2H)-yl)acetic acid;
2-(6-chloro-3-((5-chloropyrimidin-2-yl)(methyl)amino)-3,4-dihydro-1H-carbazol-9(2H)-yl)acetic acid;
2-(3-((5-chloropyrimidin-2-yl)(methyl)amino)-6-methyl-3,4-dihydro-1H-carbazol-9(2H)-yl)acetic acid;
2-(3-((5-chloropyrimidin-2-yl)(methyl)amino)-6-(trifluoromethoxy)-3,4-dihydro-1H-carbazol-9(2H)-yl)acetic acid;
2-(3-((5-chloropyrimidin-2-yl)(methyl)amino)-6-methoxy-3,4-dihydro-1H-carbazol-9(2H)-yl)acetic acid; and
2-(3-((5-chloropyrimidin-2-yl)(methyl)amino)-6-(trifluoromethyl)-3,4-dihydro-1H-carbazol-9(2H)-yl)acetic acid;
or salts (in particular pharmaceutically acceptable salts) of such compounds;
it is to be understood for any of the above listed compounds, that a stereogenic center, which is not specifically assigned, may be in absolute (R)- or absolute (S)-configuration.

Unless explicitly stated otherwise, the general terms and names used hereinbefore and hereinafter preferably have within the context of this disclosure the following meanings:

Where the plural form is used for compounds, salts, pharmaceutical compositions, diseases and the like, this is intended to mean also a single compound, salt, or the like.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

The compounds of formula (I) according to any one of embodiments 1) to 27), or pharmaceutically acceptable salts thereof, may be used for the preparation of a medicament, and are suitable for the prevention and/or treatment of diseases selected from the group consisting of chronic and acute allergic/immune diseases/disorders, comprising asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, systemic mast cell disorders, anaphylactic shock, urticaria, eczema, ulcerative colitis, chronic obstructive pulmonary disease (COPD), inflammatory bowel disease and rheumatoid arthritis; eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinophilic endocarditis (Loeffler's endocarditis), eosinophilia-myalgia syndrome, eosinophilic fasciitis, eosinophilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia and DRESS syndrome (Drug Rash with Eosinophilia and Systemic Symptoms); and basophil-related diseases, comprising basophilic leukemia and basophilic leukocytosis.

In a preferred embodiment, the compounds of formula (I) according to any one of embodiments 1) to 27), or pharmaceutically acceptable salts thereof, may be used for the preparation of a medicament, and are suitable for the prevention and/or treatment of diseases selected from the group consisting of asthma, allergic asthma, eosinophilic asthma, severe asthma, allergic rhinitis, angioedema, insect venom allergy, drug allergies, allergic sinusitis, allergic nephritis, allergic conjunctivitis, atopic dermatitis, food allergy, systemic mast cell disorders, anaphylactic shock, urticaria and eczema.

In another preferred embodiment, the compounds of formula (I) according to any one of embodiments 1) to 27), or pharmaceutically acceptable salts thereof, may be used for the preparation of a medicament, and are suitable for the prevention and/or treatment of diseases selected from the group consisting of eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinophilic endocarditis (Loeffler's endocarditis), eosinophilia-myalgia syndrome, eosinophilic fasciitis, eosinophilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia and DRESS syndrome (Drug Rash with Eosinophilia and Systemic Symptoms).

In yet another preferred embodiment, the compounds of formula (I) according to any one of embodiments 1) to 27), or pharmaceutically acceptable salts thereof, may be used for the preparation of a medicament, and are suitable for the prevention and/or treatment of diseases selected from the group consisting of basophil-related diseases, comprising basophilic leukemia and basophilic leukocytosis.

The invention also relates to the use of a compound of formula (I) according to any one of embodiments 1) to 27) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to any one of embodiments 1) to 27).

A pharmaceutical composition according to the present invention contains at least one compound of formula (I) according to any one of embodiments 1) to 27) (or a pharmaceutically acceptable salt thereof) as the active agent and optionally carriers and/or diluents and/or adjuvants.

The compounds of formula (I) according to any one of embodiments 1) to 27) and their pharmaceutically acceptable salts can be used as medicaments, e.g. in the form of pharmaceutical compositions for enteral (such as especially oral) or parenteral (including topical application or inhalation) administration.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to any one of embodiments 1) to 27), or a pharmaceutically acceptable salt thereof.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

Any reference to a compound of formula (I), ($I_{ST1}$) or ($I_{ST2}$) in this text is to be understood as referring also to the salts (and especially the pharmaceutically acceptable salts) of such compounds, as appropriate and expedient. The preferences indicated for the compounds of formula (I) of course apply mutatis mutandis to the compounds of formula ($I_{ST1}$) and the compounds of formula ($I_{ST2}$) as well as to the salts and pharmaceutically acceptable salts of the compounds of formula (I), of formula ($I_{ST1}$) or of formula ($I_{ST2}$). The same applies to these compounds as medicaments, to pharmaceutical compositions containing these compounds as active principles or to the uses of these compounds for the manufacture of a medicament for the treatment of the diseases according to this invention.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (rt) as used herein refers to a temperature of about 25° C.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range or if a variable is defined as being an integer between 1 and 4, this means that the variable is the integer 1, 2, 3, or 4.

As mentioned earlier, compounds of formula (I) modulate the PGD$_2$ activation of the CRTH2 receptor. The biological effect of such compounds may be tested in a variety of in vitro, ex vivo and in vivo assays. The ability of the compounds of formula (I) to bind to the CRTH2 receptor may be measured by methods similar to those described in the literature (Arimura A. et al., *J. Pharmacol. Exp. Ther.* 2001, 298(2), 411-419; and Sawyer N. et al., *Br. J. Pharmacol*, 2002, 137, 1163-1172, respectively) and by the assays described below in the experimental part.

A further aspect of the invention is a process for the preparation of compounds of formula (I). Compounds according to formula (I) of the present invention can be prepared according to the sequence of reactions outlined in the schemes below wherein R$^1$, R$^2$ and R$^3$ are as defined for formula (I). Other abbreviations used are defined in the experimental section. In some instances the generic groups R$^1$, R$^2$ and R$^3$ might be incompatible with the assembly illustrated in the schemes below and, therefore, will require the use of protecting groups (PG). For example it may be necessary to protect reactive functional groups such as hydroxy, amino, imino, thio or carboxy groups, where these are desired in the final product, to avoid their unwanted participation in the reactions. The use of protecting groups is well known in the art (see for example "Protective Groups in Organic Synthesis", T. W. Greene, P. G. M. Wuts, Wiley-Interscience, 1999). It will be assumed that such protecting groups are as necessary in place. In the following description, for example, PG, when used as amino-protecting group, preferably refers to a group such as tert-butoxycarbonyl, benzyloxycarbonyl, or allyloxycarbonyl, most preferably tert-butoxycarbonyl. Further, L refers to a leaving group, such as an activated hydroxy group (for example a mesylate, tosylate or a triflate) or a halogen, in particular chloro or bromo. Further, R refers to a (C$_1$-C$_4$)alkyl group, preferably methyl, ethyl or tert-butyl and most preferably ethyl.

In general, all chemical transformations can be performed according to well-known standard methodologies as described in the literature, or as described in the procedures below. The compounds obtained may also be converted into pharmaceutically acceptable salts thereof in a manner known per se.

Generally, compounds of formula (I) can be obtained from an ester derivative 2, wherein R represents (C$_1$-C$_4$)alkyl (preferably methyl, ethyl or tert-butyl and most preferably ethyl), following different synthetic routes. Compounds of formula (I) wherein R$^2$ represents hydrogen can be obtained by saponification of ester 2 with a base like LiOH, NaOH or KOH (notably NaOH) in a solvent like MeOH, EtOH, THF, acetone or MeCN (notably MeCN) in the presence or absence of water (scheme 1, method A). Alternatively (scheme 1, method B), compounds of formula (I) may be obtained by alkylation of ester derivatives 2 with an alkylating agent R$^2$—X, wherein X is a leaving group like bromide, iodide or triflate, in the presence of a base like an alkali carbonate (e.g. potassium carbonate or cesium carbonate) or sodium hydride (notably sodium hydride) in the presence of an aprotic solvent like DMF; followed by a saponification of the ester function with a base like LiOH, NaOH or KOH (notably NaOH) in the presence or absence of water. Compounds of formula (I) may also be obtained by reductive amination of an ester derivative 2 with an aldehyde R$^{2a}$—CHO, wherein "R$^{2A}$—CH$_2$" represents R$^2$, in the presence of a reducing agent like sodium cyanoborohydride in a solvent like AcOH; followed by a saponification of the ester function with a base like LiOH, NaOH or KOH (notably NaOH) in the presence or absence of water (scheme 1, method C).

Ester derivatives 2 may be prepared for instance by a microwave assisted reaction of the amine derivative 1 or its acid addition salt (e.g. HCl salt) with a heteroaryl halogenide R$^3$—X, wherein X represents for example chloride or bromide, in the presence of a base like DIEA in an aprotic solvent such as MeCN.

Scheme 1
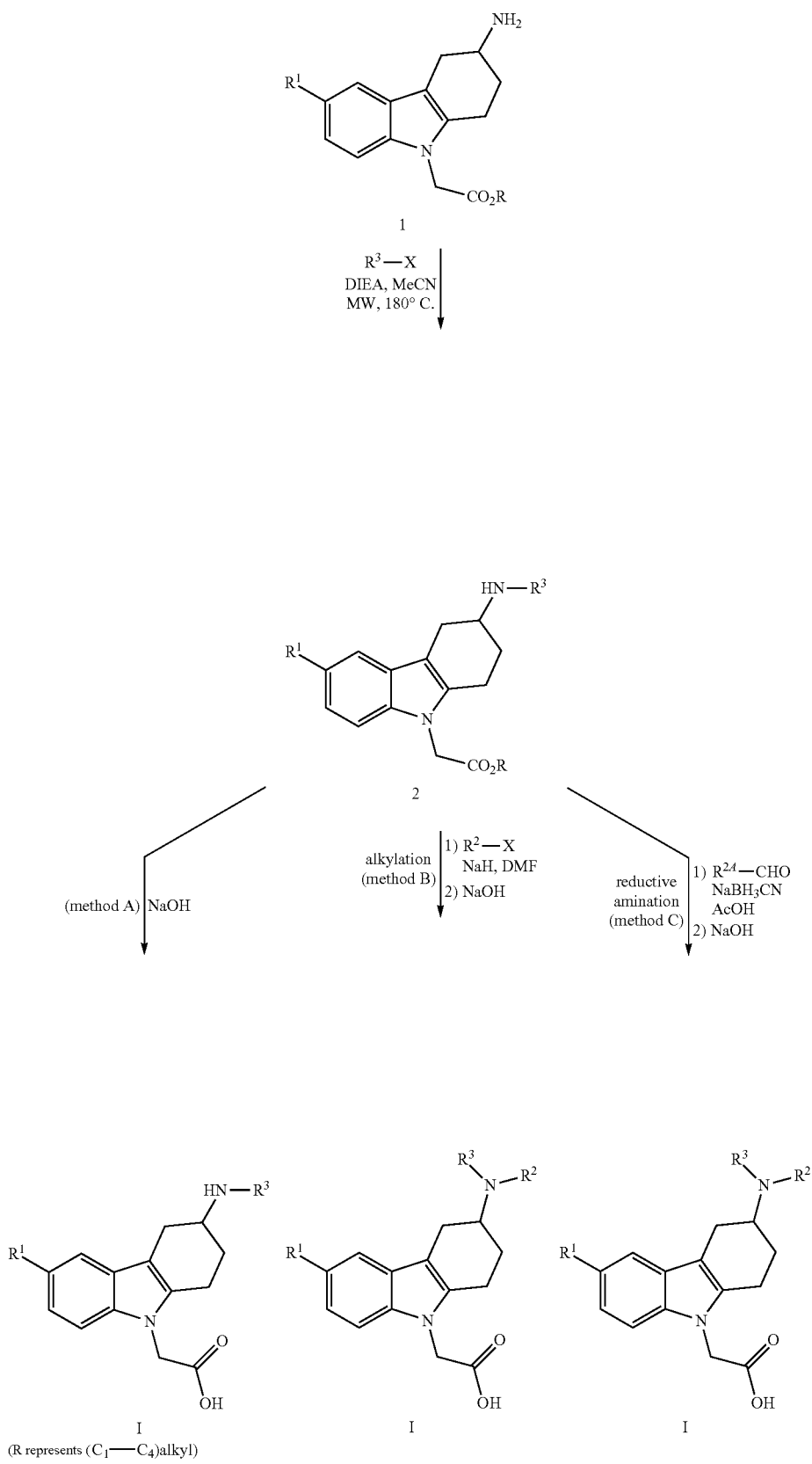

Intermediates of Structure 1 are obtained after removal of the protecting group (PG) from an intermediate of Structure 3, applying reaction conditions known to a skilled person. Preferably, the protecting group is a group such as tert-butoxycarbonyl, benzyloxycarbonyl, or allyloxycarbonyl, most preferably tert-butoxycarbonyl. A tert-butoxycarbonyl group may preferably be removed with an acid like HCl in a solvent like dioxane.

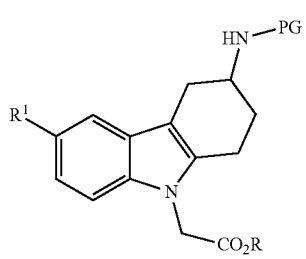

Structure 3

An intermediate of Structure 3 is generated by reacting an intermediate of Structure 4 with a compound of Formula L-CH$_2$CO$_2$R wherein R and L are as defined before, in the presence of a base, such as cesium carbonate, sodium hydride, potassium tert-butanolate or the like, in a suitable solvent, such as acetone, MeCN, THF or dioxane. Suitable L is a leaving group such as halogen (in particular bromo or chloro), mesyloxy or tosyloxy. Preferably, the compound of Formula L-CH$_2$CO$_2$R is ethyl bromoacetate.

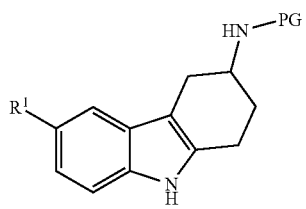

Structure 4

An intermediate of Structure 4, with PG as described hereinabove, is for instance obtained in a Fischer-type indole synthesis according to the literature (J. D. Ha et al., *Bulletin of the Korean Soc. Chem.* 2004, 25, 1784-1790): reaction of a commercially available or well known hydrazine of Structure 5 (either as a free base or as a salt) and a cyclohexanone of Structure 6, which is commercially available or whose synthesis is as described in the above mentioned literature, furnishes the desired intermediate of Structure 4 as a racemate.

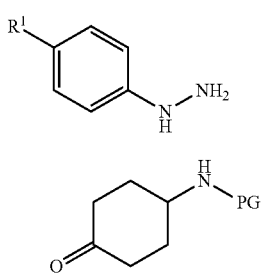

Structure 5

6

In another aspect, an intermediate of Structure 4 is obtained through protection of the amino group in a tetrahydrocarbazol-3-ylamine of Structure 7 with a hereinabove described protecting group applying methods known to a skilled person. For example, the amino-group of the intermediate of structure 7 may be Boc-protected by reaction with Boc$_2$O in the presence of a base such as DIEA and a catalytic amount of DMAP or dimethylaminoethylamine (preferred) in an aprotic solvent such as DCM.

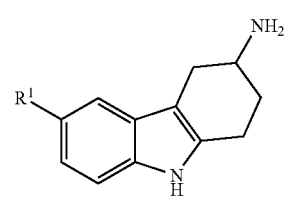

Structure 7

Both, the (R)- and the (S)-enantiomer of starting tetrahydrocarbazol-3-ylamine of Structure 7 are obtained in a stereospecific reaction following a procedure described in literature (Rosentreter U. et al., *Arzneim.-Forsch.* 1989, 39(12), 1519-1521; and EP 0242518).

A synthesis of racemic ethyl (3RS)-(3-amino-1,2,3,4-tetrahydro-9H-carbazol-9-yl)acetate hydrochloride is described in the literature (Ulven, T.; Kostenis, E. *J. Med. Chem.* 2005, 48, 897-900).

A stereoselective synthesis of methyl (3R)-(3-tert-butoxycarbonylamino-1,2,3,4-tetrahydro-9H-carbazol-9-yl)-acetate is described in WO 03/097598.

Whenever the compounds of formula (I) or an intermediate of structures 1 to 4 or 7 are obtained in the form of mixtures of enantiomers, the enantiomers may be separated using methods known to the one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as Et$_3$N and/or diethylamine) and eluent B (hexane), at a flow rate of 0.8 to 150 mL/min.

EXPERIMENTAL SECTION

Abbreviations (as Used Herein)

AcOH Acetic acid
aq. Aqueous
APC Allophycocyanin
Bdg Binding
Boc tert-butoxycarbonyl
BSA Bovine Serum Albumin
DCM Dichloromethane
DIEA N,N-Diisopropylethylamine
DMF Dimethylformamide
DMAP 4-dimethylaminopyridine
DMSO Dimethylsulfoxide
dpm decays per minute
EA Ethyl acetate
EDTA Ethylene Diamine Tetraacetic Acid
ESI-MS Electrospray Ionization Mass Spectroscopy
Et Ethyl
h Hour(s)
HEPES 4-(2-hydroxyethyl)-1-piperazineethanesulfonic acid
HPLC High Performance Liquid Chromatography
HSA Human Serum Albumin l Liter(s)
LC-MS Liquid Chromatography-Mass Spectroscopy
MeCN Acetonitrile
MeOH Methanol
min Minute(s)
Me Methyl
MS Mass Spectroscopy
MW Microwave
N Normality of solution
NMR Nuclear magnetic resonance
PBS Phosphate Buffered Saline
PEI Polyethyleneimine
PG Protecting group
$PGD_2$ Prostaglandin $D_2$
rt Room temperature
s Second(s)
TEA Triethylamine
Tf Trifluoromethanesulfonyl
TFA Trifluoroacetic acid
THF Tetrahydrofuran
$t_R$ Retention time
Tris Tris-(hydroxymethyl)aminomethane buffer
Vol Volume

CHEMISTRY

General Remarks

All solvents and reagents are used as obtained from commercial sources unless otherwise indicated.

Temperatures are indicated in degrees Celsius (° C.). Unless otherwise indicated, the reactions take place at room temperature (rt).

In mixtures, relations of parts of solvent or eluent or reagent mixtures in liquid form are given as volume relations (v/v), unless indicated otherwise.

Analytical HPLC Conditions as Used in the Examples Below:

HPLC/MS analyses are performed on a Waters 2795 Alliance HPLC instrument, equipped with a Waters 996 Photodiode Array Detector and a Micromass ZQ™ Waters mass spectrometer (electron spray ionization), detection at 200-400 nm (LC-3), or on a Agilent 1100 system, equipped with a Dionex P580 binary pump, a Dionex PDA-100 Photodiode Array Detector and a Finnigan AQA mass spectrometer (LC-1 and LC-2).

The LC retention times are obtained using the following elution conditions:

LC-1: Analytical HPLC on a Ascentis Express MS C18 column (4.6×30 mm, Waters); Linear gradient of water/ 0.04% TFA (A) and MeCN (B) from 5% to 95% B over 1.5 min; flow rate 4.5 ml/min, detection at 210 nm.

LC-2: Analytical HPLC on a Zorbax® SB-AQ column (4.6×50 mm, 5 µm, Agilent); Linear gradient of water/ 0.04% TFA (A) and MeCN (B) from 5% to 95% B over 1.5 min; flow rate 4.5 ml/min, detection at 210 nm.

LC-3: Analytical HPLC on a Agilent SB C-18 column, (1.8 µm, 2.1×50 mm), Linear gradient of water/0.04% TFA (A) and MeCN (B) from 5% to 95% B over 1.5 min., flow rate 4.5 ml/min, detection at 210 nm.

Preparative HPLC/MS purifications are performed on a Gilson 333/334 binary high pressure gradient pump system with a Gilson 215 autosampler and fraction collector, a Dionex UVD340U DAD detector, a polymerlabs PL-ELS 1000 ELS detector and a Finnigan AQA MS detector or a Thermo MSQ Plus MS detector, using a Waters Atlantis T3 column (10 µm, 30×75 mm), with a linear gradient of MeCN (A) and water/0.5% formic acid (B) over 5 min.; flow rate 75 ml/min.

$^1$H-NMR spectra are recorded either on a Varian Mercury 300VX FT-NMR spectrometer or on a Bruker Advance II 400 spectrometer. Chemical shifts (δ) are reported in parts per million (ppm) relative to proton resonances resulting from incomplete deuteration of the NMR solvent, e.g. for DMSO δ(H) 2.49 ppm, and the abbreviations s, d, t, q, m and br refer to singlet, doublet, triplet, quartet, multiplet, and broad, respectively.

Analytical HPLC over a chiral stationary phase are performed on a Daicel ChiralPak IA (4.6×250 mm, 5 µm) column. Typical conditions of chiral HPLC are an isocratic mixture of 80% heptane and 20% EtOH, at a flow rate of 0.8 mL/min., detection at 210 nm (chiral HPLC-1).

Preparative HPLC over a chiral stationary phase are performed on a Daicel ChiralPak AD-H (20×250 mm, 5 µm) column. Typical conditions of chiral HPLC are an isocratic mixture of 50% EtOH and 50% hexane, at a flow rate of 16 mL/min., detection at 210 nm (chiral HPLC-2).

A.1 Synthesis of enantiomerically enriched 2,3,4,9-tetrahydro-1H-carbazol-3-amine derivatives A.1.1 Synthesis of 6-fluoro-1,2,4,9-tetrahydrospiro [carbazole-3,2'-[1,3]dioxolane]

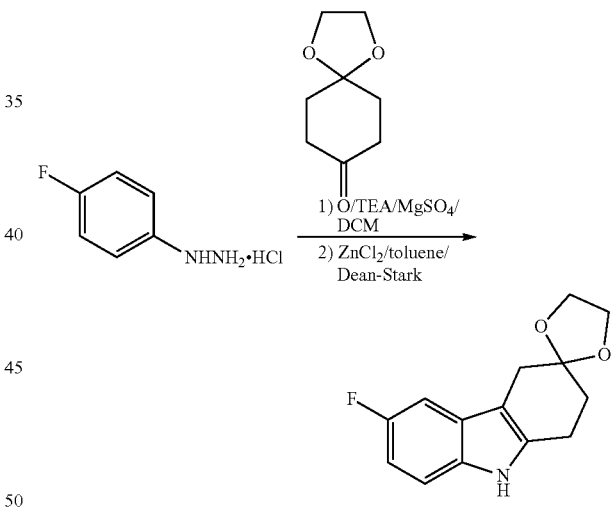

To a suspension of $MgSO_4$ (18.4 g, 0.154 mol) in DCM (500 ml) were added 1,4-dioxaspiro[4.5]decan-8-one (48.0 g, 0.308 mol) and 4-fluorophenylhydrazine hydrochloride (50.0 g, 0.308 mol). Then, TEA (43.8 ml, 0.308 mol) was added dropwise over 5 min. The internal temperature went up from 17° C. to 25° C. upon addition of TEA. The resulting suspension was allowed to stir at rt for 4 h and filtered. The white solid was washed twice with DCM and the filtrate was concentrated in reduced pressure. The orange slurry was suspended in toluene (500 ml) and $ZnCl_2$ (38.6 g, 0.283 mol) was added. The resulting dark orange solution was stirred at reflux using a Dean-Stark apparatus for 12 h. After cooling to rt, the resulting black mixture was filtered over celite. The solid was washed with isopropyl acetate, the organic filtrate was basified with 1N NaOH (until pH ~12). The aqueous phase was extracted with isopropyl acetate, the combined organic extracts were passed through celite, dried over Na₂SO₄, filtered and concentrated in vacuo to yield the titled compound as a dark brown solid.

LC-MS (LC-2): t$_R$: 0.80 min./[M+H]⁺: 248.19.

A.1.2 Synthesis of 6-fluoro-4,9-dihydro-1H-carbazol-3-(2H)-one

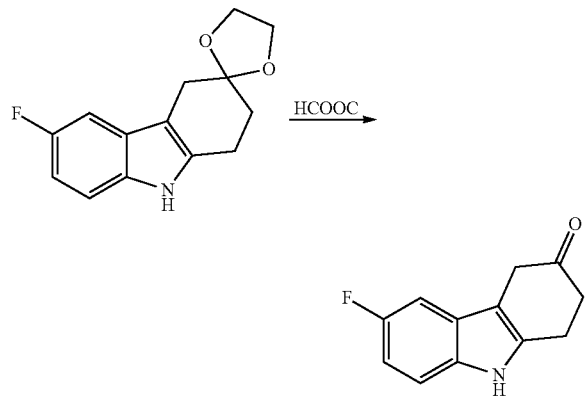

A solution of 6-fluoro-1,2,4,9-tetrahydrospiro[carbazole-3,2'-[1,3]dioxolane] (33.7 g, 0.136 mol) in formic acid (123 ml) was stirred at rt for 4 h30. Then water was added carefully at 0° C., the resulting suspension was stirred for 30 min at 0-5° C. The suspension was filtered off and the yellow solid was washed twice with water (2×14 ml), dried in high vacuum overnight to yield the titled compound as a yellow solid.

¹H-NMR (DMSO-d₆): δ 2.75 (m, 2H); 3.15 (m, 2H); 3.5 (s, 2H); 6.85 (m, 1H); 7.1 (dd, 1H); 7.25 (m, 1H); 11.05 (s, 1H).

A.1.3 Synthesis of (S)-6-fluoro-N—((R)-1-phenylethyl)-2,3,4,9-tetrahydro-1H-carbazol-3-amine

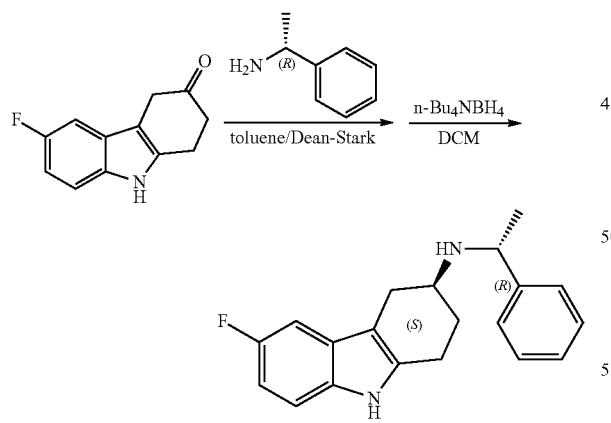

A mixture of 6-fluoro-4,9-dihydro-1H-carbazol-3-(2H)-one (15 g, 0.074 mol) and (R)-α-methylbenzylamine (9.6 ml, 0.074 mol) in dry toluene (100 ml) was stirred at reflux for 5 h using a Dean-Stark apparatus. After cooling to rt, the reaction mixture was concentrated in vacuo to give the crude imine which was used for the next step without further purification (highly unstable with air).

To a cold (−50° C.) solution of tetra-n-butylammonium tetrahydridoborate (20.9 g, 0.081 mol) in dry DCM (80 ml) was added dropwise over 2 h a solution of the previous imine (22.6 g, 0.074 mol) in dry DCM (80 ml). After complete addition, the reaction mixture was allowed to warm-up to 15° C. overnight. Then was added slowly (over 30 min.) at 4° C. 2NH₂SO₄ (40 ml), a solid started to precipitate. 10 ml more of 2NH₂SO₄ was added and the mixture was stirred at 4° C. for 45 min. The solid was filtered off, washed with water and dried in vacuum to yield a crude slightly brownish solid. This solid was dissolved in a mixture of isopropyl acetate (135 ml), MeOH (40 ml) and 1N NaOH (135 ml) and the mixture was stirred vigorously for 45 min., the solution became brown/purple. If the solid had not entirely dissolved, more iPrOAc/MeOH/NaOH (1 vol each) were added. The layers were separated and the aqueous phase was extracted with EA. The combined organic phases were dried over Na₂SO₄, filtered and concentrated to the half volume. To this solution was added MeOH (35 ml) and cooled to 4° C. and was added dropwise 4N HCl in dioxane (0.45 vol) and the mixture was stirred at 4° C. for 1 h. The resulting precipitate was filtered off and dried in vacuum to yield the HCl salt as white crystals. This solid was suspended in a mixture of EA (80 ml), MeOH (45 ml), and 1N NaOH (80 ml) was added, the resulting clear yellow solution was stirred for 20 min. The layers were separated and the aqueous phase was extracted with EA. The combined organic phases were dried over Na₂SO₄, filtered and concentrated in vacuo to afford 8.96 g (35%, de 95/5) of the title compound as a white solid.

LC-MS (LC-3): t$_R$: 3.63 min./[M+H]⁺: 309.2.

Comment: The assignment of the stereogenic center at the 3-position of the obtained 2,3,4,9-tetrahydro-1H-carbazol-3-amine derivative was done in analogy to Rosentreter U. et al., *Arzneim.-Forsch*. 1989, 39(12), 1519-1521.

A.1.4 Synthesis of (R)-6-fluoro-N—((S)-1-phenylethyl)-2,3,4,9-tetrahydro-1H-carbazol-3-amine

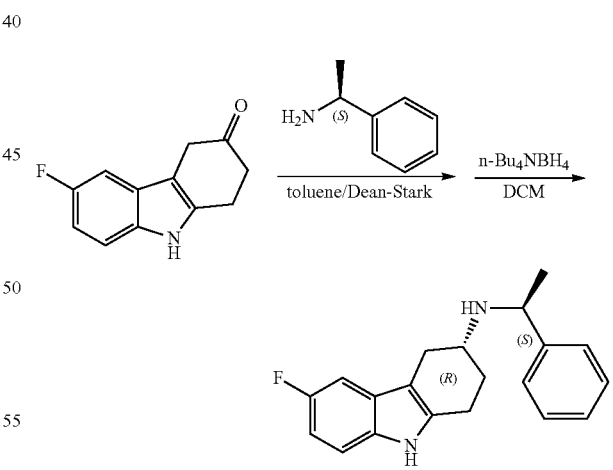

By following the same procedure as (S)-6-fluoro-N—((R)-1-phenylethyl)-2,3,4,9-tetrahydro-1H-carbazol-3-amine but using (S)-α-methylbenzylamine for the reductive amination, the title compound was obtained as a white solid.

LC-MS (LC-3): t$_R$: 4.01 min./[M+H]⁺: 309.2.

Comment: The assignment of the stereogenic center at the 3-position of the obtained 2,3,4,9-tetrahydro-1H-carbazol-3- amine derivative was done in analogy to Rosentreter U. et al., *Arzneim.-Forsch.* 1989, 39(12), 1519-1521.

A.1.5 Synthesis of (S)-6-fluoro-2,3,4,9-tetrahydro-1H-carbazol-3-amine

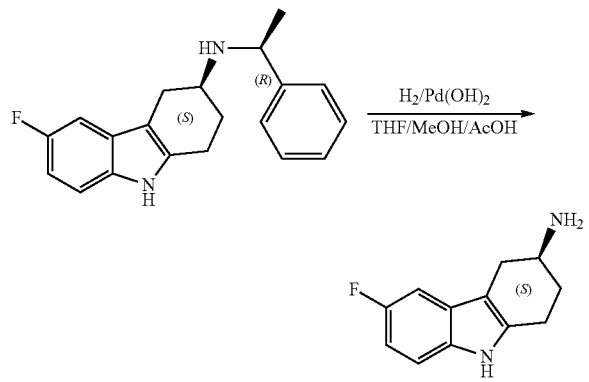

To a degassed solution of (S)-6-fluoro-N—((R)-1-phenylethyl)-2,3,4,9-tetrahydro-1H-carbazol-3-amine (8.96 g, 0.029 mol) in a mixture of THF (60 ml), MeOH (20 ml) and AcOH (10 ml) was added 20% Pd(OH)$_2$ (1.34 g). The mixture was evacuated three times and the reaction was set under 1 atm (balloon) H$_2$. It was stirred at rt for 10 h and filtered over celite. The pad was rinsed with THF/MeOH and the filtrate was concentrated to 50 ml. The residue was dissolved in EA, and washed with 1N NaOH. The aqueous phase was extracted with EA and the combined organic phases were dried over Na$_2$SO$_4$, filtered and concentrated in vacuo to afford the title compound as a white solid.

LC-MS (LC-2): $t_R$: 0.64 min./[M+H+MeCN]$^+$: 246.19

HPLC (chiral HPLC-1): $t_R$: 36.9 min (S-isomer); $t_R$: 40.0 min (R-isomer); (ee: 93.6%).

A.1.6 Synthesis of (R)-6-fluoro-2,3,4,9-tetrahydro-1H-carbazol-3-amine

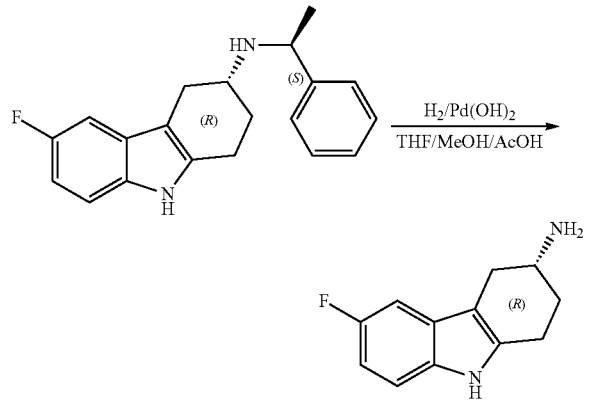

Following the same procedure as (S)-6-fluoro-2,3,4,9-tetrahydro-1H-carbazol-3-amine, hydrogenation of (R)-6-fluoro-N—((S)-1-phenylethyl)-2,3,4,9-tetrahydro-1H-carbazol-3-amine (8.7 g, 0.028 mol) gave the title compound as a white solid.

LC-MS (LC-2): $t_R$: 0.64 min./[M+H+MeCN]$^+$: 246.19

HPLC (chiral HPLC-1): $t_R$: 37.1 min (S-isomer); $t_R$: 39.2 min (R-isomer); (ee: 94.2%).

A.1.7 Synthesis of (S)-tert-butyl (6-fluoro-2,3,4,9-tetrahydro-1H-carbazol-3-yl)carbamate

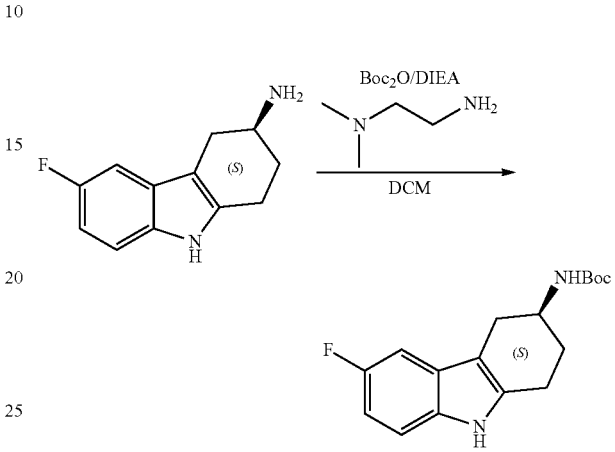

To a solution of (S)-6-fluoro-2,3,4,9-tetrahydro-1H-carbazol-3-amine (5.2 g, 0.025 mol) and Boc$_2$O (6.66 g, 0.030 mol) in dry DCM (120 ml) was added DIEA (5.56 ml, 0.032 mol). After stirring at rt for 1 h45, dimethylaminoethylamine (0.66 g, 7.7 mmol) was added. The stirring at rt was continued for 15 min, the reaction mixture was diluted in sat. aq. NH$_4$Cl solution. The aqueous phase was extracted twice with DCM, the combined organic extracts were dried over Na$_2$SO$_4$, filtered and concentrated in vacuo to afford a crude solid.

FC (EA/n-heptane: 1/1) gave the title compound as a light brown foam.

LC-MS (LC-2): $t_R$: 0.99 min./[M+H]$^+$: 305.44.

A.1.8 Synthesis of (R)-tert-butyl (6-fluoro-2,3,4,9-tetrahydro-1H-carbazol-3-yl)carbamate

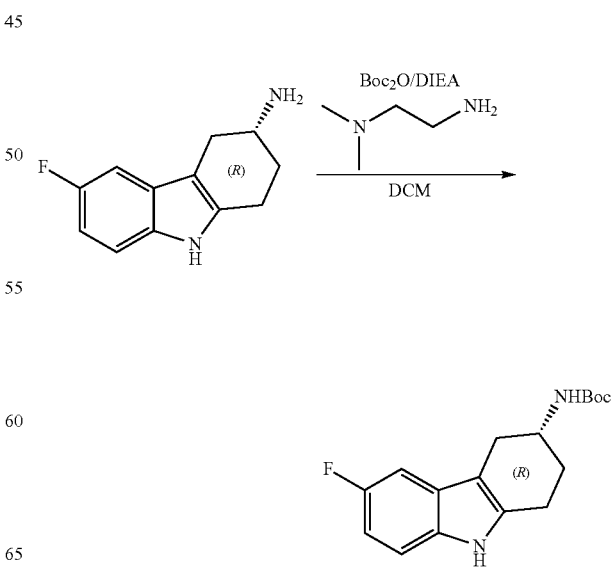

Following the same procedure as (S)-tert-butyl (6-fluoro-2,3,4,9-tetrahydro-1H-carbazol-3-yl)carbamate, the title compound was obtained as a light brown foam.
LC-MS (LC-2): $t_R$: 1.00 min./[M+H]$^+$: 305.12.

A.1.9 Synthesis of (S)-ethyl 2-(3-((tert-butoxycarbonyl)amino)-6-fluoro-3,4-dihydro-1H-carbazol-9(2H)-yl)acetate

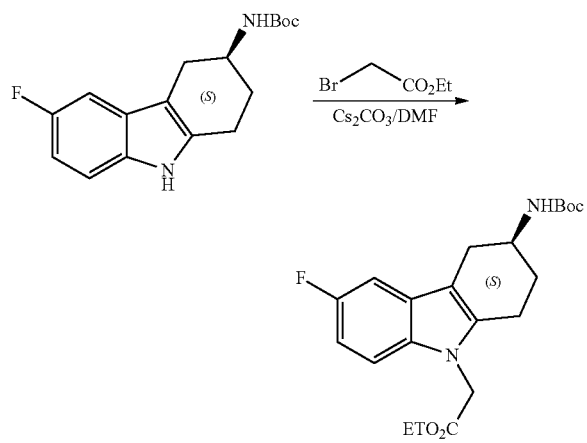

A solution of ethyl bromoacetate (3.08 ml, 0.027 mol) in dry DMF (35 ml) was added dropwise to a mixture of (S)-tert-butyl (6-fluoro-2,3,4,9-tetrahydro-1H-carbazol-3-yl)carbamate (6.5 g, 0.021 mol) and Cs$_2$CO$_3$ (20.5 g, 0.063 mol) in dry DMF (145 ml). The resulting reaction mixture was stirred at 65° C. for 2 h and then at rt overnight. The reaction mixture was poured into water and extracted with EA. The combined organic extracts were washed with water, brine, dried over Na$_2$SO$_4$, filtered and concentrated in vacuo to give a crude yellow solid.

FC (EA/n-heptane: 1/1) gave the titled compound as a pale yellow solid.
LC-MS (LC-2): $t_R$: 1.04 min./[M+H]$^+$: 391.5.

A.1.10 Synthesis of (R)-ethyl 2-(3-((tert-butoxycarbonyl)amino)-6-fluoro-3,4-dihydro-1H-carbazol-9(2H)-yl)acetate

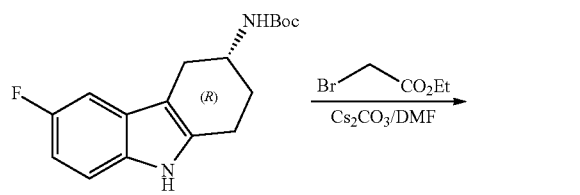

Following the same procedure as (S)-ethyl 2-(3-((tert-butoxycarbonyl)amino)-6-fluoro-3,4-dihydro-1H-carbazol-9(2H)-yl)acetate, the title compound was obtained as a white foam.
LC-MS (LC-2): $t_R$: 1.06 min./[M+H]$^+$: 391.16.

A.1.11 Synthesis of (S)-ethyl 2-(3-amino-6-fluoro-3,4-dihydro-1H-carbazol-9(2H)-yl)acetate hydrochloride

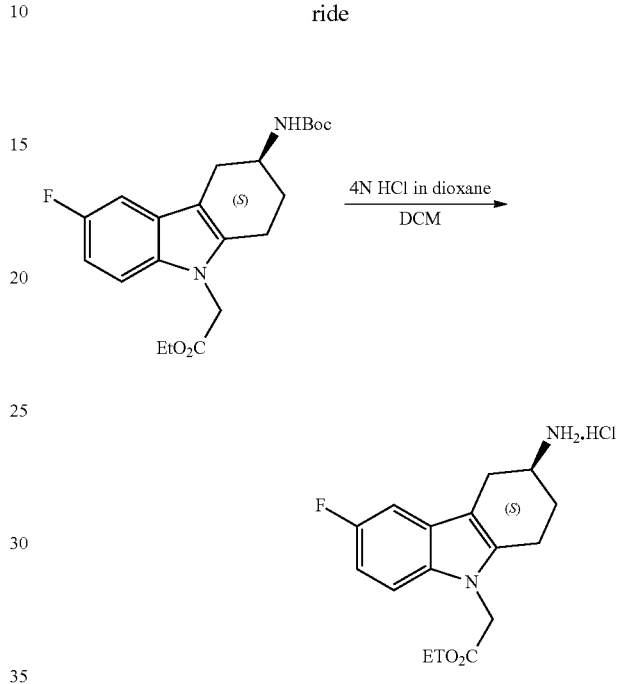

To a cold (0° C.) solution of (S)-ethyl 2-(3-((tert-butoxycarbonyl)amino)-6-fluoro-3,4-dihydro-1H-carbazol-9(2H)-yl)acetate (8.2 g, 0.021 mol) in dry DCM (50 ml) was added dropwise 4N HCl in dioxane (52.5 ml, 0.21 mol). The resulting reaction mixture was stirred at 0° C. for 2 h and then at rt for 5 h. The reaction mixture was concentrated in vacuo and the resulting solid was dissolved in EtOH (70 ml) and was added at 0° C. 3N HCl in EA (7 ml). The reaction mixture was stirred at reflux overnight. After cooling to rt, the reaction mixture was concentrated in vacuo to afford the title compound as a beige powder.
LC-MS (LC-2): $t_R$: 0.63 min./[M+H]$^+$: 291.08.

A.1.12 Synthesis of (R)-ethyl 2-(3-amino-6-fluoro-3,4-dihydro-1H-carbazol-9(2H)-yl)acetate hydrochloride

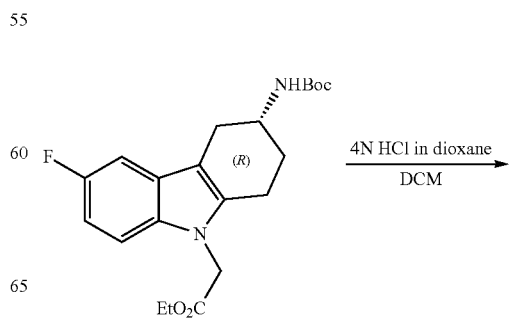

27
-continued

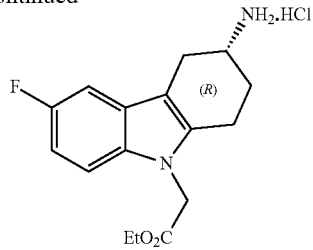

Following the same procedure as (S)-ethyl 2-(3-amino-6-fluoro-3,4-dihydro-1H-carbazol-9(2H)-yl)acetate hydrochloride, the title compound was obtained as a beige solid.

LC-MS (LC-2): $t_R$: 0.64 min./[M+H]$^+$: 291.16

A.1.13 Synthesis of benzyl (6-fluoro-2,3,4,9-tetrahydro-1H-carbazol-3-yl)carbamate

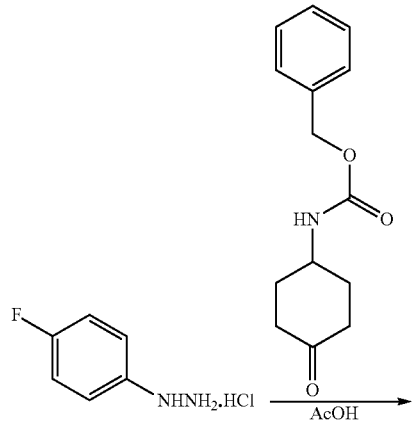

A solution of benzyl (4-oxocyclohexyl)carbamate (21.7 g, 87.8 mmol) and 4-fluorophenylhydrazine hydrochloride (14.3 g, 87.8 mmol) in glacial AcOH (148 ml) was stirred at reflux for 1 h30. After cooling to rt, the reaction mixture was diluted with EA and washed with sat.aq. NaHCO$_3$ solution. The aqueous phase was extracted twice with EA, the combined organic extracts were washed with sat. aq. NaHCO$_3$ solution, water and brine, dried over MgSO$_4$, filtered and concentrated in vacuo to give the title compound as a light brown foam which was used for the next step without further purification.

LC-MS (LC-1): $t_R$: 0.83 min./[M+H]$^+$: 339.25.

28
A.1.14 Synthesis of ethyl 2-(3-(((benzyloxy)carbonyl)amino)-6-fluoro-3,4-dihydro-1H-carbazol-9(2H)-yl)acetate

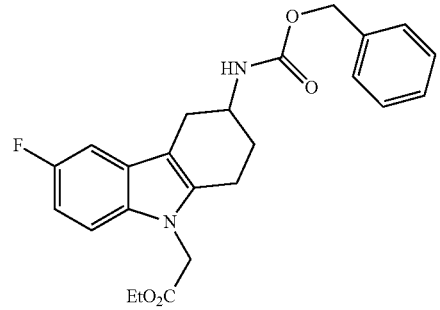

To a solution of benzyl (6-fluoro-2,3,4,9-tetrahydro-1H-carbazol-3-yl)carbamate (29.8 g, 87.9 mmol) in acetone (252 ml) was added Cs$_2$CO$_3$ (71.6 g, 219.8 mmol). The resulting light brown suspension was stirred at rt for 10 min., then ethyl bromoacetate (19.5 ml, 176 mmol) was added dropwise. The reaction mixture was stirred at rt for 48 h, poured into water and extracted with EA. The combined organic extracts were washed with water and brine, dried over MgSO$_4$, filtered and concentrated in vacuo to give a crude solid.

FC (EA/n-heptane: 1/1) gave the title compound as a white solid.

LC-MS (LC-2): $t_R$: 0.88 min./[M+H]$^+$: 425.26.

The two enantiomers of the obtained product were separated by preparative chiral HPLC:
(S)-ethyl 2-(3-(((benzyloxy)carbonyl)amino)-6-fluoro-3,4-dihydro-1H-carbazol-9(2H)-yl)acetate: HPLC (chiral HPLC-2): $t_R$: 8.42 min;
(R)-ethyl 2-(3-(((benzyloxy)carbonyl)amino)-6-fluoro-3,4-dihydro-1H-carbazol-9(2H)-yl)acetate: HPLC (chiral HPLC-2): $t_R$: 10.38 min.

A.1.15 Synthesis of (S)-ethyl 2-(3-amino-6-fluoro-3,4-dihydro-1H-carbazol-9(2H)-yl)acetate hydrochloride

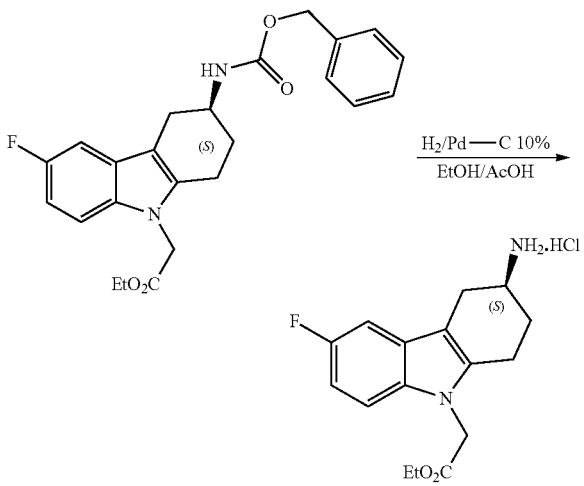

Pd—C (10%, 419 mg) was added to a stirred degassed suspension of (S)-ethyl 2-(3-(((benzyloxy)carbonyl)amino)-6-fluoro-3,4-dihydro-1H-carbazol-9(2H)-yl)acetate (1.67 g, 3.93 mmol) in a mixture of EtOH (10.5 ml) and glacial AcOH (45 ml). The reaction mixture was set under 1 atm (balloon) H$_2$ and stirred at rt for 1 h30. The reaction mixture was filtered over a pad of celite and the celite was washed with DCM. 4N HCl in dioxane (9.75 ml) was added to the filtrate which was then concentrated in vacuo. The resulting solid was triturated with diethyl ether, filtered and the solid was rinsed with diethyl ether, dried in vacuo to afford the title compound as a white powder.

LC-MS (LC-2): $t_R$: 0.64 min./[M+H]$^+$: 291.21.

A.1.16 Synthesis of (R)-ethyl 2-(3-amino-6-fluoro-3,4-dihydro-1H-carbazol-9(2H)-yl)acetate hydrochloride

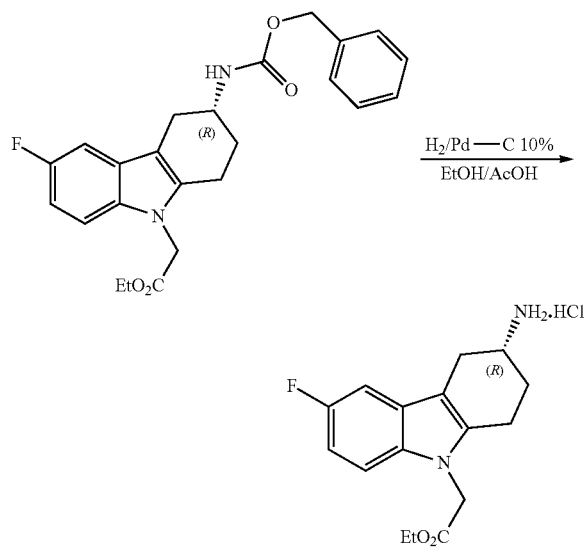

Following the same procedure as (S)-ethyl 2-(3-amino-6-fluoro-3,4-dihydro-1H-carbazol-9(2H)-yl)acetate hydrochloride but using (R)-ethyl 2-(3-(((benzyloxy)carbonyl) amino)-6-fluoro-3,4-dihydro-1H-carbazol-9(2H)-yl)acetate, the title compound was obtained as a white solid.

LC-MS (LC-2): $t_R$: 0.66 min./[M+H]$^+$: 291.08.

A.1.17 Synthesis of (3S)- and (3R)-ethyl 2-(3-heteroarylamino-3,4-dihydro-1H-carbazol-9-(2H)-yl) acetate derivative (General Procedure)

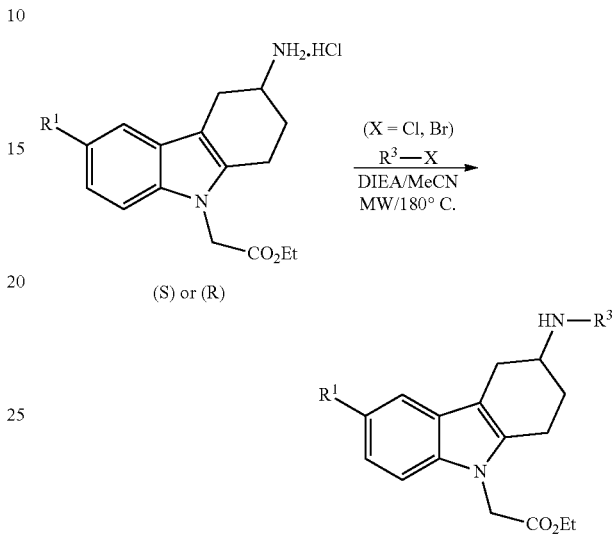

A mixture of the respective (3S)-ethyl 2-(3-amino-3,4-dihydro-1H-carbazol-9-(2H)-yl) acetate hydrochloride derivative (0.122 mmol), DIEA (0.306 mmol, 2.5 eq) and the appropriate halide derivative R$^3$—X (0.122 mmol) in dry MeCN (1 mL) was irradiated in a microwave oven at 180° C. for 20 min. After cooling to rt, the products were directly purified by prep. HPLC to provide the desired compound.

In analogy, the other enantiomers were prepared starting from the respective (3R)-ethyl 2-(3-amino-3,4-dihydro-1H-carbazol-9-(2H)-yl)acetate hydrochloride derivative.

Preparation of Intermediates

The following (3S)- and (3R)-ethyl 2-(3-heteroarylamino-3,4-dihydro-1H-carbazol-9-(2H)-yl)acetate derivatives were synthesized according to the above general procedure (X as used for the halide derivative R$^3$—X represents chloride):

TABLE 1

| Intermediate | Name | [M + H]$^+$ m/z | $t_R$ [min] LC-MS method |
|---|---|---|---|
| 1 | (3S)-ethyl 2-(6-fluoro-3-((5-fluoropyrimidin-2-yl)amino)-3,4-dihydro-1H-carbazol-9-(2H)-yl)acetate | 387.02 | 0.89 LC-2 |
| 2 | (3R)-ethyl 2-(6-fluoro-3-((5-fluoropyrimidin-2-yl)amino)-3,4-dihydro-1H-carbazol-9-(2H)-yl)acetate | 386.94 | 0.78 LC-2 |
| 3 | (3S)-ethyl 2-(6-fluoro-3-((5-chloropyrimidin-2-yl)amino)-3,4-dihydro-1H-carbazol-9-(2H)-yl)acetate | 402.74 | 0.92 LC-2 |
| 4 | (3R)-ethyl 2-(6-fluoro-3-((5-chloropyrimidin-2-yl)amino)-3,4-dihydro-1H-carbazol-9-(2H)-yl)acetate | 402.86 | 0.88 LC-2 |
| 5 | (3S)-ethyl 2-(6-fluoro-3-((5-(trifluoromethyl)pyrimidin-2-yl)amino)-3,4-dihydro-1H-carbazol-9-(2H)-yl)acetate | 437.20 | 0.93 LC-1 |

TABLE 1-continued

| Intermediate | Name | [M + H]+ m/z | t_R [min] LC-MS method |
|---|---|---|---|
| 6 | (3R)-ethyl 2-(6-fluoro-3-((5-(trifluoromethyl)pyrimidin-2-yl)amino)-3,4-dihydro-1H-carbazol-9-(2H)-yl)acetate | 437.07 | 0.90 LC-2 |
| 7 | (3S)-ethyl 2-(6-fluoro-3-((4-(trifluoromethyl)pyrimidin-2-yl)amino)-3,4-dihydro-1H-carbazol-9-(2H)-yl)acetate | 437.20 | 0.94 LC-1 |
| 8 | (3R)-ethyl 2-(6-fluoro-3-((4-(trifluoromethyl)pyrimidin-2-yl)amino)-3,4-dihydro-1H-carbazol-9-(2H)-yl)acetate | 437.14 | 0.91 LC-2 |
| 9 | (3S)-ethyl 2-(6-fluoro-3-(pyrimidin-2-ylamino)-3,4-dihydro-1H-carbazol-9(2H)-yl)acetate | 369.19 | 0.66 LC-1 |
| 10 | (3S)-ethyl 2-(3-((4,6-dimethylpyrimidin-2-yl)amino)-6-fluoro-3,4-dihydro-1H-carbazol-9(2H)-yl)acetate | 397.02 | 0.76 LC-2 |
| 11 | (3S)-ethyl 2-(6-fluoro-3-((4-methylpyrimidin-2-yl)amino)-3,4-dihydro-1H-carbazol-9(2H)-yl)acetate | 383.24 | 0.64 LC-1 |
| 12 | (3S)-ethyl 2-(3-((5-chlorobenzo[d]oxazol-2-yl)amino)-6-fluoro-3,4-dihydro-1H-carbazol-9(2H)-yl)acetate | 442.17 | 0.92 LC-1 |
| 13 | (3S)-ethyl 2-(3-(benzo[d]oxazol-2-ylamino)-6-fluoro-3,4-dihydro-1H-carbazol-9(2H)-yl)acetate | 408.21 | 0.77 LC-1 |
| 14 | (3S)-ethyl 2-(3-(benzo[d]thiazol-2-ylamino)-6-fluoro-3,4-dihydro-1H-carbazol-9(2H)-yl)acetate | 424.21 | 0.73 LC-1 |
| 15 | (3S)-ethyl 2-(6-fluoro-3-(quinazolin-4-ylamino)-3,4-dihydro-1H-carbazol-9(2H)-yl)acetate | 419.23 | 0.63 LC-1 |
| 16 | (3S)-ethyl 2-(6-fluoro-3-((2-(trifluoromethyl)quinazolin-4-yl)amino)-3,4-dihydro-1H-carbazol-9(2H)-yl)acetate | 487.18 | 0.96 LC-1 |
| 17 | (3S)-ethyl 2-(6-fluoro-3-((2-methylquinazolin-4-yl)amino)-3,4-dihydro-1H-carbazol-9(2H)-yl)acetate | 433.11 | 0.66 LC-1 |
| 18 | (3S)-ethyl 2-(6-fluoro-3-(quinazolin-2-ylamino)-3,4-dihydro-1H-carbazol-9(2H)-yl)acetate | 418.99 | 0.79 LC-2 |
| 19 | (3S)-ethyl 2-(6-fluoro-3-((5-fluorobenzo[d]oxazol-2-yl)amino)-3,4-dihydro-1H-carbazol-9(2H)-yl)acetate | 426.01 | 0.94 LC-2 |
| 20 | (3S)-ethyl 2-(6-fluoro-3-((5-phenylpyrimidin-2-yl)amino)-3,4-dihydro-1H-carbazol-9(2H)-yl)acetate | 445.19 | 0.96 LC-2 |
| 21 | (3S)-ethyl 2-(6-fluoro-3-((5-methoxypyrimidin-2-yl)amino)-3,4-dihydro-1H-carbazol-9(2H)-yl)acetate | 399.24 | 0.75 LC-1 |
| 22 | (3S)-ethyl 2-(3-((6-chlorobenzo[d]thiazol-2-yl)amino)-6-fluoro-3,4-dihydro-1H-carbazol-9(2H)-yl)acetate | 458.04 | 0.95 LC-2 |
| 23 | (3S)-ethyl 2-(3-((5-chlorobenzo[d]thiazol-2-yl)amino)-6-fluoro-3,4-dihydro-1H-carbazol-9(2H)-yl)acetate | 458.06 | 0.96 LC-2 |
| 24 | (3S)-ethyl 2-(6-fluoro-3-((5-(trifluoromethyl)pyridin-2-yl)amino)-3,4-dihydro-1H-carbazol-9(2H)-yl)acetate | 436.09 | 0.88 LC-2 |
| 25 | (3S)-ethyl 2-(6-fluoro-3-((5-fluoropyridin-2-yl)amino)-3,4-dihydro-1H-carbazol-9(2H)-yl)acetate | 385.72 | 0.75 LC-2 |
| 26 | (3S)-ethyl 2-(3-((5-chloropyridin-2-yl)amino)-6-fluoro-3,4-dihydro-1H-carbazol-9(2H)-yl)acetate | 401.79 | 0.80 LC-2 |
| 27 | (3S)-ethyl 2-(6-fluoro-3-((6-fluorobenzo[d]thiazol-2-yl)amino)-3,4-dihydro-1H-carbazol-9(2H)-yl)acetate | 442.08 | 0.88 LC-2 |
| 28 | (3S)-ethyl 2-(6-fluoro-3-((5-fluorobenzo[d]thiazol-2-yl)amino)-3,4-dihydro-1H-carbazol-9(2H)-yl)acetate | 441.97 | 0.90 LC-2 |
| 29 | (3S)-ethyl 2-(3-((6-chlorobenzo[d]oxazol-2-yl)amino)-6-fluoro-3,4-dihydro-1H-carbazol-9(2H)-yl)acetate | 442.01 | 0.97 LC-2 |
| 30 | (3S)-ethyl 2-(3-((5-cyclopropylpyrimidin-2-yl)amino)-6-fluoro-3,4-dihydro-1H-carbazol-9-(2H)-yl)acetate | 409.22 | 0.85 LC-2 |
| 31 | (3S)-ethyl 2-(6-fluoro-3-((6-fluorobenzo[d]oxazol-2-yl)amino)-3,4-dihydro-1H-carbazol-9(2H)-yl)acetate | 426.23 | 0.93 LC-2 |
| 32 | (3S)-ethyl 2-(6-fluoro-3-(quinoxalin-2-ylamino)-3,4-dihydro-1H-carbazol-9(2H)-yl)acetate | 419.16 | 0.79 LC-2 |

A.2 Synthesis of racemic 2,3,4,9-tetrahydro-1H-carbazol-3-amine derivatives

A.2.1 Synthesis of benzyl (2,3,4,9-tetrahydro-1H-carbazol-3-yl)carbamate derivatives

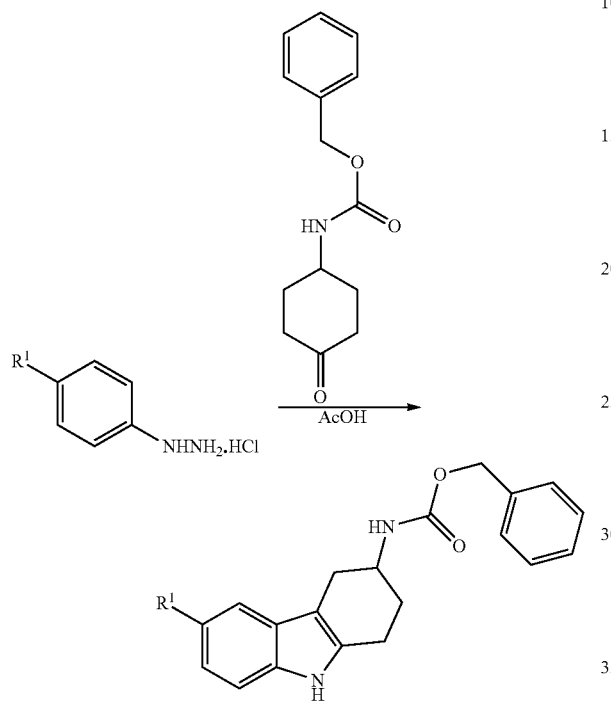

A solution of benzyl (4-oxocyclohexyl)carbamate (1 g, 4 mmol) and the respective 4-substituted arylhydrazine hydrochloride derivative (1 eq) in glacial AcOH (6.8 ml) was stirred at reflux for 1 h30. After cooling to rt, the reaction mixture was diluted with EA and washed with sat. aq. NaHCO$_3$ solution. The aqueous phase was extracted twice with EA, the combined organic extracts were washed with sat. aq. NaHCO$_3$ solution, water and brine, dried over MgSO$_4$, filtered and concentrated in vacuo to give the title compound as a foam which was used for the next step without further purification.

The following benzyl (2,3,4,9-tetrahydro-1H-carbazol-3-yl)carbamate derivatives were synthesized according to the above general procedure

TABLE 2

| R$^1$ | Name | [M + H]$^+$ m/z | $t_R$ [min] LC-MS method |
|---|---|---|---|
| H | benzyl (2,3,4,9-tetrahydro-1H-carbazol-3-yl)carbamate | 321.2 | 0.91 LC-2 |
| Cl | benzyl (6-chloro-2,3,4,9-tetrahydro-1H-carbazol-3-yl)carbamate | 355.11 | 0.94 LC-2 |
| Me | benzyl (6-methyl-2,3,4,9-tetrahydro-1H-carbazol-3-yl)carbamate | 335.15 | 0.93 LC-2 |
| OCF$_3$ | benzyl (6-(trifluoromethoxy)-2,3,4,9-tetrahydro-1H-carbazol-3-yl)carbamate | 405.1 | 0.97 LC-2 |
| OCH$_3$ | benzyl (6-methoxy-2,3,4,9-tetrahydro-1H-carbazol-3-yl)carbamate | 351.16 | 0.89 LC-2 |

TABLE 2-continued

| R$^1$ | Name | [M + H]$^+$ m/z | $t_R$ [min] LC-MS method |
|---|---|---|---|
| CF$_3$ | benzyl (6-(trifluoromethyl)-2,3,4,9-tetrahydro-1H-carbazol-3-yl)carbamate | 389.09 | 0.96 LC-2 |
| F | benzyl (6-fluoro-2,3,4,9-tetrahydro-1H-carbazol-3-yl)carbamate | 339.25 | 0.83 LC-1 |

A.2.2 Synthesis of ethyl 2-(3-(((benzyloxy)carbonyl)amino)-3,4-dihydro-1H-carbazol-9(2H)-yl)acetate derivatives

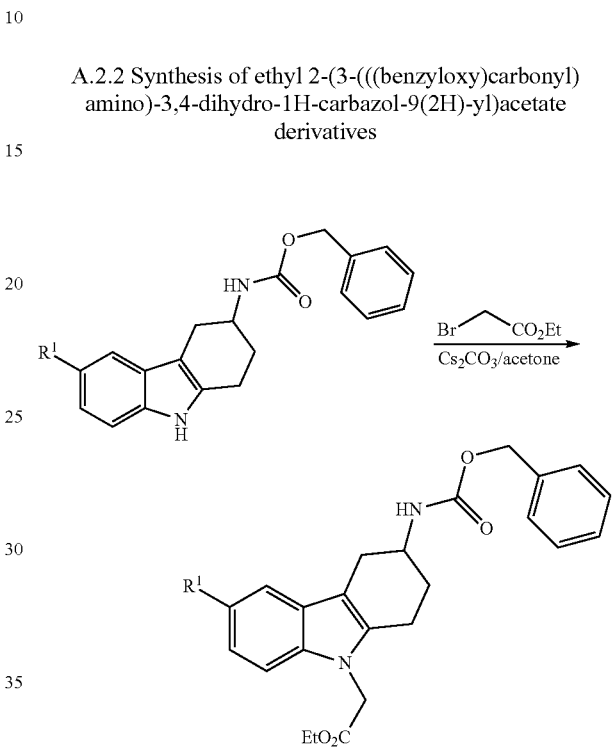

To a solution of the respective benzyl (2,3,4,9-tetrahydro-1H-carbazol-3-yl)carbamate derivative (4 mmol) in acetone (11.5 ml) was added Cs$_2$CO$_3$ (10 mmol, 2.5 eq). The resulting light brown suspension was stirred at rt for 10 min., then ethyl bromoacetate (8 mmol, 2 eq) was added dropwise. The reaction mixture was stirred at rt for 48 h, poured into water and extracted with EA. The combined organic extracts were washed with water and brine, dried over MgSO$_4$, filtered and concentrated in vacuo to give a crude solid.

FC (EA/n-heptane: 1/1) gave the title compound as a white solid.

The following ethyl 2-(3-(((benzyloxy)carbonyl)amino)-3,4-dihydro-1H-carbazol-9(2H)-yl)acetate derivatives were synthesized according to the above general procedure

TABLE 3

| R$^1$ | Name | [M + H]$^+$ m/z | $t_R$ [min] LC-MS method |
|---|---|---|---|
| H | ethyl 2-(3-(((benzyloxy)carbonyl)amino)-3,4-dihydro-1H-carbazol-9(2H)-yl)acetate | 407.15 | 0.96 LC-2 |
| Cl | ethyl 2-(3-(((benzyloxy)carbonyl)amino)-6-chloro-3,4-dihydro-1H-carbazol-9(2H)-yl)acetate | 441.12 | 0.99 LC-2 |
| Me | ethyl 2-(3-(((benzyloxy)carbonyl)amino)-6-methyl-3,4-dihydro-1H-carbazol-9(2H)-yl)acetate | 421.18 | 0.99 LC-2 |

TABLE 3-continued

| R¹ | Name | [M + H]⁺ m/z | $t_R$ [min] LC-MS method |
|---|---|---|---|
| OCF₃ | ethyl 2-(3-(((benzyloxy)carbonyl)amino)-6-(trifluoromethoxy)-3,4-dihydro-1H-carbazol-9(2H)-yl)acetate | 491.14 | 1.01 LC-2 |
| OCH₃ | ethyl 2-(3-(((benzyloxy)carbonyl)amino)-6-methoxy-3,4-dihydro-1H-carbazol-9(2H)-yl)acetate | 437.17 | 0.95 LC-2 |
| CF₃ | ethyl 2-(3-(((benzyloxy)carbonyl)amino)-6-(trifluoromethyl)-3,4-dihydro-1H-carbazol-9(2H)-yl)acetate | 475.18 | 1.01 LC-2 |
| F | ethyl 2-(3-(((benzyloxy)carbonyl)amino)-6-fluoro-3,4-dihydro-1H-carbazol-9(2H)-yl)acetate | 425.26 | 0.88 LC-2 |

A.2.3 Synthesis of ethyl 2-(3-amino-3,4-dihydro-1H-carbazol-9(2H)-yl)acetate hydrobromide derivatives

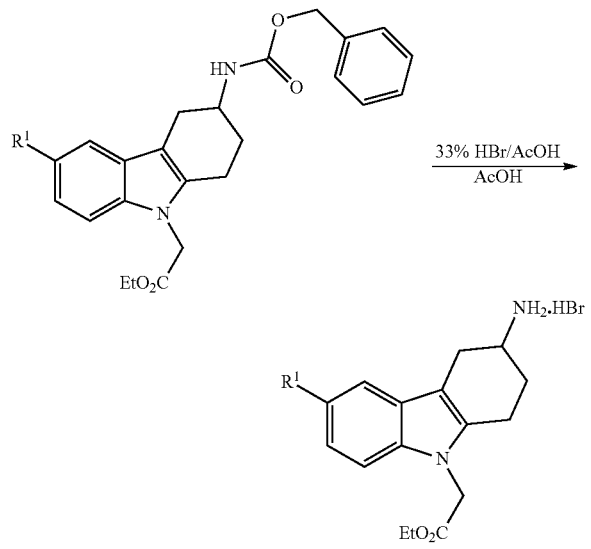

To a solution of the respective ethyl 2-(3-(((benzyloxy)carbonyl)amino)-3,4-dihydro-1H-carbazol-9(2H)-yl)acetate derivative (500 mg) in glacial AcOH (12 ml) was added 33% HBr in AcOH (3 ml). The reaction mixture was stirred at rt for 1 h and then concentrated in vacuo to give a crude oil. Trituration with a mixture of diethyl ether/DCM (9/1) gave the title compound as a solid The following ethyl 2-(3-amino-3,4-dihydro-1H-carbazol-9(2H)-yl) acetate hydrobromide derivatives were synthesized according to the above general procedure

TABLE 4

| R¹ | Name | [M + H]⁺ m/z | $t_R$ [min] LC-MS method |
|---|---|---|---|
| H | ethyl 2-(3-amino-3,4-dihydro-1H-carbazol-9(2H)-yl)acetate hydrobromide | 273.22 | 0.61 LC-2 |
| Cl | ethyl 2-(3-amino-6-chloro-3,4-dihydro-1H-carbazol-9(2H)-yl)acetate hydrobromide | 307.08 | 0.66 LC-2 |
| Me | ethyl 2-(3-amino-6-methyl-3,4-dihydro-1H-carbazol-9(2H)-yl)acetate hydrobromide | 287.18 | 0.65 LC-2 |
| OCF₃ | ethyl 2-(3-amino-6-(trifluoromethoxy)-3,4-dihydro-1H-carbazol-9(2H)-yl)acetate hydrobromide | 357.16 | 0.71 LC-2 |
| OCH₃ | ethyl 2-(3-amino-6-methoxy-3,4-dihydro-1H-carbazol-9(2H)-yl)acetate hydrobromide | 303.21 | 0.61 LC-2 |
| CF₃ | ethyl 2-(3-amino-6-(trifluoromethyl)-3,4-dihydro-1H-carbazol-9(2H)-yl)acetate hydrobromide | 341.15 | 0.69 LC-2 |
| F | ethyl 2-(3-amino-6-fluoro-3,4-dihydro-1H-carbazol-9(2H)-yl)acetate hydrobromide | 291.12 | 0.61 LC-2 |

A.2.4 Synthesis of ethyl 2-(3-oxo-3,4-dihydro-1H-carbazol-9(2H)-yl)acetate derivatives

A.2.4.1 Preparation of ethyl 2-(1,2-dihydrospiro[carbazole-3,2'-[1,3]dioxolan]-9(4H)-yl)acetate derivatives

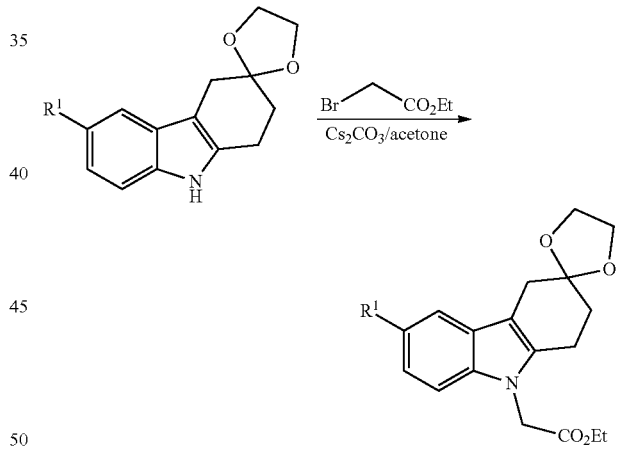

General Procedure:

To a solution of the appropriate 1,2,4,9-tetrahydrospiro[carbazole-3,2'-[1,3]dioxolane] derivative (prepared as for 6-fluoro-1,2,4,9-tetrahydrospiro[carbazole-3,2'-[1,3]dioxolane]) (20 mmol) in dry acetone (65 mL), was added Cs₂CO₃ (2.5 eq). The resulting suspension was stirred at rt for 10 min. under argon, and then was added ethyl bromoacetate (2 eq). The reaction was stirred for 2 days under argon, filtered over celite and the cake was washed with acetone. The filtrate was concentrated in vacuo and the residue was poured into water. The aqueous phase was extracted with EA, the combined organic extracts were dried over MgSO₄, filtered and concentrated in vacuo to give a crude oil.

FC (EA/n-heptane: 1/1) gave the title compound as a solid.

The following ethyl 2-(1,2-dihydrospiro[carbazole-3,2'-[1,3]dioxolan]-9(4H)-yl)acetate derivative was synthesized according to the above general procedure:

Ethyl 2-(6-fluoro-1,2-dihydrospiro[carbazole-3,2'-[1,3]dioxolan]-9-(4H)-yl)acetate LC-MS (LC-2): $t_R$: 0.89 min./[M+H]$^+$: 334.12.

A.2.4.2 Preparation of ethyl 2-(3-oxo-3,4-dihydro-1H-carbazol-9(2H)-yl)acetate derivatives

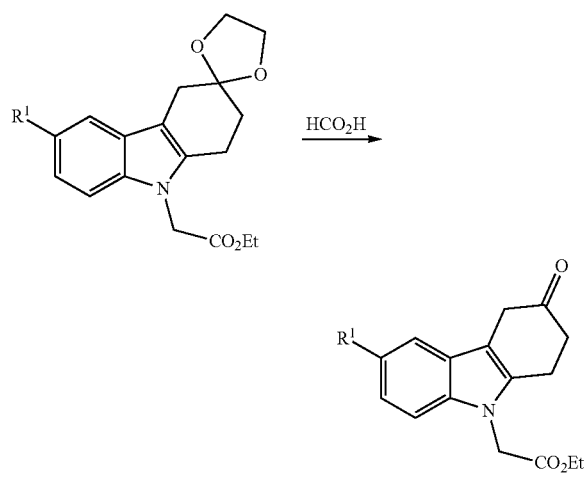

General Procedure:

A solution of the respective ethyl 2-(1,2-dihydrospiro[carbazole-3,2'-[1,3]dioxolan]-9(4H)-yl)acetate derivative (20 mmol) in neat formic acid (17 mL) was stirred at rt for 4 h30 under argon. The reaction mixture was then cooled to 4° C. and quenched by the addition of water (2 mL). The resulting suspension was stirred for 30 min. and then filtered. The solid was then dried in high vacuum.

The following ethyl 2-(3-oxo-3,4-dihydro-1H-carbazol-9(2H)-yl) acetate derivative was synthesized according to the above general procedure:

Ethyl 2-(6-fluoro-3-oxo-3,4-dihydro-1H-carbazol-9(2H)-yl)acetate

LC-MS (LC-2): $t_R$: 0.85 min./[M+H]$^+$: 290.02.

A.2.5 Synthesis of ethyl 2-(3-heteroarylamino-3,4-dihydro-1H-carbazol-9-(2H)-yl)acetate derivatives General Procedure A (Via Reductive Amination):

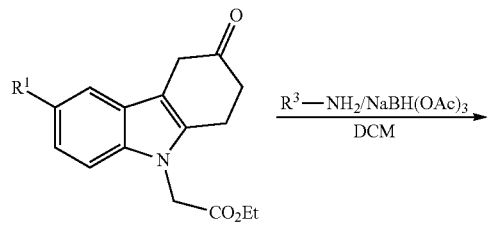

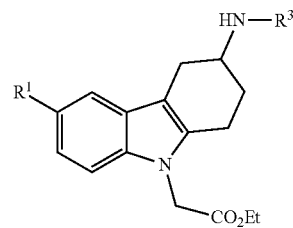

To a mixture of the respective ethyl 2-(3-oxo-3,4-dihydro-1H-carbazol-9(2H)-yl) acetate derivative (50 mg), R$^3$—NH$_2$ (1.1 eq) in dry DCM (1 mL) was added NaBH(OAc)$_3$ (2.2 eq). The reaction mixture was stirred at rt overnight and poured into sat. NaHCO$_3$ solution. The organic layer was dried over anhydrous MgSO$_4$, filtered and concentrated in vacuo to give a crude oil. The products were purified by prep. HPLC to provide the desired compound.

The following ethyl 2-(3-heteroarylamino-3,4-dihydro-1H-carbazol-9-(2H)-yl)acetate derivatives were synthesized according to the above general procedure A:

TABLE 5

| Intermediate | Name | [M + H]$^+$ m/z | $t_R$ [min] LC-MS method |
|---|---|---|---|
| 33 | ethyl 2-(6-fluoro-3-((4-methylthiazol-2-yl)amino)-3,4-dihydro-1H-carbazol-9(2H)-yl)acetate | 388.14 | 0.74 LC-2 |
| 34 | ethyl 2-(3-((4-(tert-butyl)thiazol-2-yl)amino)-6-fluoro-3,4-dihydro-1H-carbazol-9(2H)-yl)acetate | 430.07 | 0.82 LC-2 |
| 35 | ethyl 2-(6-fluoro-3-((4-(trifluoromethyl)-thiazol-2-yl)amino)-3,4-dihydro-1H-carbazol-9(2H)-yl)acetate | 442.12 | 0.99 LC-2 |
| 36 | ethyl 2-(3-((5-(tert-butyl)isoxazol-3-yl)amino)-6-fluoro-3,4-dihydro-1H-carbazol-9(2H)-yl)acetate | 414.23 | 0.98 LC-2 |
| 37 | ethyl 2-(6-fluoro-3-((1-methyl-1H-pyrazol-3-yl)amino)-3,4-dihydro-1H-carbazol-9(2H)-yl)acetate | 371.12 | 0.75 LC-1 |
| 38 | ethyl 2-(6-fluoro-3-((5-methyl-1,3,4-thiadiazol-2-yl)amino)-3,4-dihydro-1H-carbazol-9(2H)-yl)acetate | 389.09 | 0.8 LC-2 |
| 39 | ethyl 2-(6-fluoro-3-(isoxazol-3-ylamino)-3,4-dihydro-1H-carbazol-9(2H)-yl)acetate | 358.08 | 0.88 LC-1 |
| 40 | ethyl 2-(6-fluoro-3-((5-methylisoxazol-3-yl)amino)-3,4-dihydro-1H-carbazol-9(2H)-yl)acetate | 372.15 | 0.9 LC-2 |

General Procedure B (Via Alkylation):

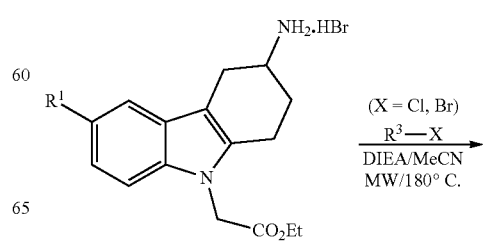

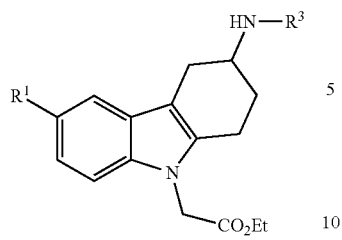

A mixture of the respective ethyl 2-(3-amino-3,4-dihydro-1H-carbazol-9-(2H)-yl) acetate hydrobromide derivative (0.122 mmol), DIEA (0.306 mmol, 2.5 eq) and the appropriate halide derivative $R^3$—X (0.122 mmol) in dry MeCN (1 mL) was irradiated in a microwave oven at 180° C. for 20 min. After cooling to rt, the products were directly purified by prep. HPLC to provide the desired compound.

The following ethyl 2-(3-heteroarylamino-3,4-dihydro-1H-carbazol-9-(2H)-yl)acetate derivatives were synthesized according to the above general procedure B (X as used for the halide derivative $R^3$—X represents chloride):

TABLE 6

| Intermediate | Name | [M + H]$^+$ m/z | $t_R$ [min] LC-MS method |
|---|---|---|---|
| 41 | ethyl 2-(3-((5-chloropyrimidin-2-yl)-amino)-3,4-dihydro-1H-carbazol-9(2H)-yl)acetate | 385.09 | 0.89 LC-2 |
| 42 | ethyl 2-(6-chloro-3-((5-chloropyrimidin-2-yl)amino)-3,4-dihydro-1H-carbazol-9(2H)-yl)acetate | 419.03 | 0.78 LC-2 |
| 43 | ethyl 2-(3-((5-chloropyrimidin-2-yl)amino)-6-methyl-3,4-dihydro-1H-carbazol-9(2H)-yl)acetate | 399.07 | 0.92 LC-2 |
| 44 | ethyl 2-(3-((5-chloropyrimidin-2-yl)amino)-6-(trifluoromethoxy)-3,4-dihydro-1H-carbazol-9(2H)-yl)acetate | 469.06 | 0.88 LC-2 |
| 45 | ethyl 2-(3-((5-chloropyrimidin-2-yl)amino)-6-methoxy-3,4-dihydro-1H-carbazol-9(2H)-yl)acetate | 415.08 | 0.93 LC-1 |
| 46 | ethyl 2-(3-((5-chloropyrimidin-2-yl)amino)-6-(trifluoromethyl)-3,4-dihydro-1H-carbazol-9(2H)-yl)acetate | 453.08 | 0.90 LC-2 |

B. Synthesis of Final Compounds of Formula (I) (General Procedure)

1) Method A (for Compounds of Formula (I) Wherein $R^2$ Represents Hydrogen) (Via Saponification)

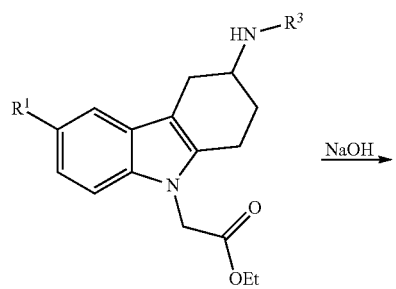

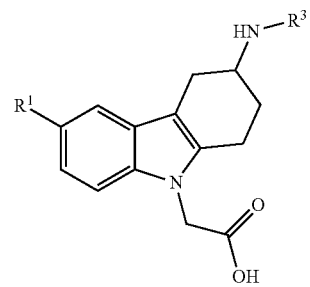

To a solution of the respective -ethyl 2-(3-heteroarylamino-3,4-dihydro-1H-carbazol-9-(2H)-yl)acetate derivative (0.15 mmol) in MeCN (1 mL), was added 1N NaOH (0.4 mL, 0.4 mmol). The reaction mixture was stirred at rt for 1 h, then was added at 0° C. 37% HCl (0.1 mL). The products were directly purified by prep. HPLC to provide the final compound.

2) Method B (Via Alkylation)

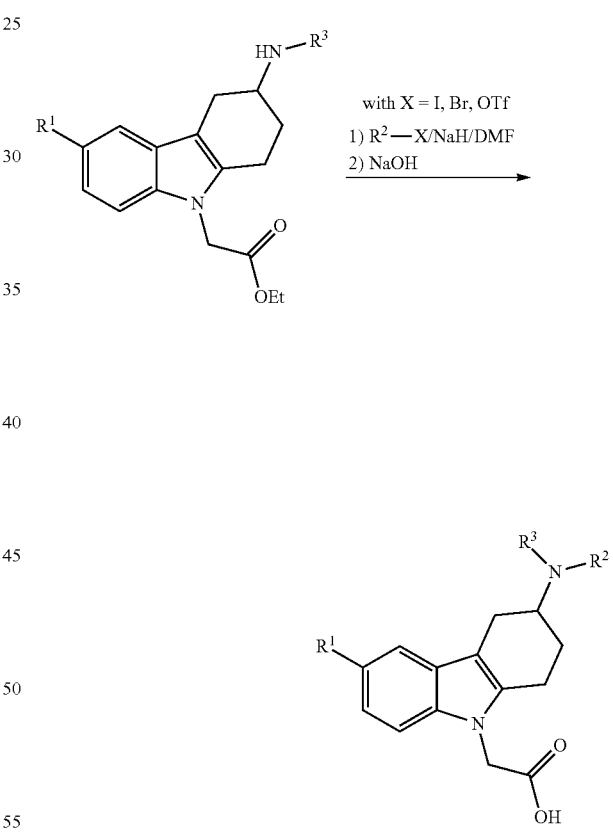

To a cold (0° C.) solution of the respective -ethyl 2-(3-heteroarylamino-3,4-dihydro-1H-carbazol-9-(2H)-yl)acetate derivative (0.06 mmol) in dry DMF (0.6 mL), was added NaH (0.12 mmol, 2 eq). The reaction mixture was stirred at 0° C. for 30 min., then was added the appropriate halide derivative ($R^2$—X) (0.24 mmol, 4 eq). The reaction mixture was stirred at rt for 3 h. 1N NaOH (5.5 eq) was added and the mixture was stirred at rt for 1 h and then 37% HCl was added until pH 1-2. The products were directly purified by prep. HPLC to provide the final compound.

3) Method C (Via Reductive Amination)

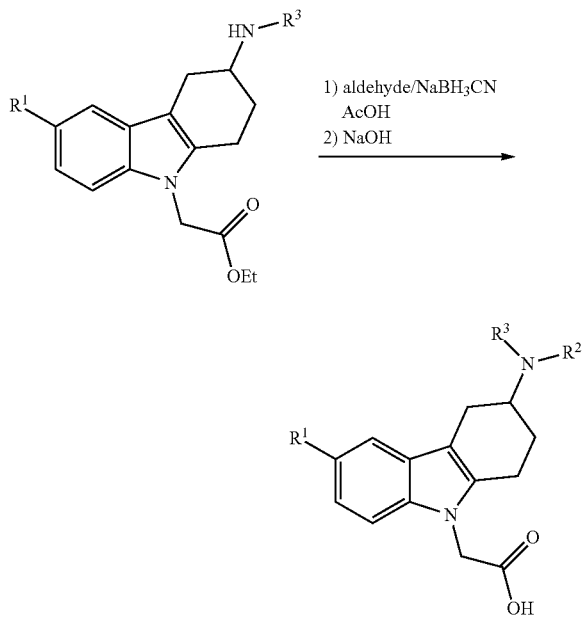

To a mixture of the respective -ethyl 2-(3-heteroarylamino-3,4-dihydro-1H-carbazol-9-(2H)-yl)acetate derivative (0.045 mmol) and the appropriate aldehyde (10 eq) in glacial AcOH (0.4 mL), was added portionwise NaBH$_3$CN (10 eq). The reaction mixture was stirred at rt for 45 min., then additional NaBH$_3$CN (10 eq) was added and the stirring at rt was continued for 30 min. Then 30% aq NaOH was added until pH 9-10 and the mixture was stirred at rt overnight. Then water and 37% HCl (until pH 1-2) were added and the reaction mixture was extracted with DCM. The combined organic extracts were dried (MgSO$_4$), filtered and concentrated in vacuo to give the crude acid. The products were directly purified by prep. HPLC to provide the final compound.

Preparation of Examples

The following 2-(3-heteroarylamino-3,4-dihydro-1H-carbazol-9-(2H)-yl) acetic acid derivatives were synthesized according to the above general procedures (X as used for the halide derivative R$^2$—X of method B represents iodide exept for example 27 and 34 (X=Br) and for example 41 (X=OTf)):

TABLE 7

| Example Method | Name | [M + H]$^+$ m/z | $t_{R\,[min.]}$ LC-MS method |
|---|---|---|---|
| 1 method A | (3S)-2-(6-fluoro-3-((5-fluoropyrimidin-2-yl)amino)-3,4-dihydro-1H-carbazol-9-(2H)-yl)acetic acid | 359.15 | 0.67 LC-2 |
| 2 method A | (3R)-2-(6-fluoro-3-((5-fluoropyrimidin-2-yl)amino)-3,4-dihydro-1H-carbazol-9-(2H)-yl)acetic acid | 359.20 | 0.67 LC-2 |
| 3 method A | (3S)-2-(6-fluoro-3-((5-chloropyrimidin-2-yl)amino)-3,4-dihydro-1H-carbazol-9-(2H)-yl)acetic acid | 375.15 | 0.76 LC-1 |
| 4 method A | (3R)-2-(6-fluoro-3-((5-chloropyrimidin-2-yl)amino)-3,4-dihydro-1H-carbazol-9-(2H)-yl)acetic acid | 375.03 | 0.77 LC-2 |
| 5 method A | (3R)-2-(6-fluoro-3-((5-(trifluoromethyl)pyrimidin-2-yl)amino)-3,4-dihydro-1H-carbazol-9-(2H)-yl)acetic acid | 409.13 | 0.80 LC-2 |
| 6 method A | (3R)-2-(6-fluoro-3-((4-(trifluoromethyl)pyrimidin-2-yl)amino)-3,4-dihydro-1H-carbazol-9-(2H)-yl)acetic acid | 409.13 | 0.81 LC-2 |
| 7 method B | (3S)-2-(6-fluoro-3-((5-fluoropyrimidin-2-yl)(methyl)amino)-3,4-dihydro-1H-carbazol-9(2H)-yl)acetic acid | 373.08 | 0.87 LC-2 |
| 8 method B | (3R)-2-(6-fluoro-3-((5-fluoropyrimidin-2-yl)(methyl)amino)-3,4-dihydro-1H-carbazol-9(2H)-yl)acetic acid | 373.26 | 0.74 LC-2 |
| 9 method B | (3S)-2-(3-((5-chloropyrimidin-2-yl)(methyl)amino)-6-fluoro-3,4-dihydro-1H-carbazol-9(2H)-yl)acetic acid | 388.94 | 0.90 LC-2 |
| 10 method B | (3R)-2-(3-((5-chloropyrimidin-2-yl)(methyl)amino)-6-fluoro-3,4-dihydro-1H-carbazol-9(2H)-yl)acetic acid | 389.13 | 0.83 LC-2 |
| 11 method B | (3S)-2-(6-fluoro-3-(methyl(5-(trifluoromethyl)pyrimidin-2-yl)amino)-3,4-dihydro-1H-carbazol-9(2H)-yl)acetic acid | 423.13 | 0.91 LC-1 |
| 12 method B | (3R)-2-(6-fluoro-3-(methyl(5-(trifluoromethyl)pyrimidin-2-yl)amino)-3,4-dihydro-1H-carbazol-9(2H)-yl)acetic acid | 423.18 | 0.86 LC-2 |
| 13 method B | (3S)-2-(6-fluoro-3-(methyl(4-(trifluoromethyl)pyrimidin-2-yl)amino)-3,4-dihydro-1H-carbazol-9(2H)-yl)acetic acid | 423.17 | 0.89 LC-1 |
| 14 method B | (3R)-2-(6-fluoro-3-(methyl(4-(trifluoromethyl)pyrimidin-2-yl)amino)-3,4-dihydro-1H-carbazol-9(2H)-yl)acetic acid | 423.08 | 0.87 LC-2 |

TABLE 7-continued

| Example Method | Name | [M + H]+ m/z | $t_{R\ [min.]}$ LC-MS method |
|---|---|---|---|
| 15 method B | (3S)-2-(6-fluoro-3-(methyl(pyrimidin-2-yl)amino)-3,4-dihydro-1H-carbazol-9(2H)-yl)acetic acid | 355.23 | 0.59 LC-1 |
| 16 method B | (3S)-2-(3-((4,6-dimethylpyrimidin-2-yl)(methyl)amino)-6-fluoro-3,4-dihydro-1H-carbazol-9(2H)-yl)acetic acid | 382.98 | 0.61 LC-2 |
| 17 method B | (3S)-2-(6-fluoro-3-(methyl(4-methylpyrimidin-2-yl)amino)-3,4-dihydro-1H-carbazol-9(2H)-yl)acetic acid | 369.17 | 0.57 LC-1 |
| 18 method B | (3S)-2-(3-((5-chlorobenzo[d]oxazol-2-yl)(methyl)amino)-6-fluoro-3,4-dihydro-1H-carbazol-9(2H)-yl)acetic acid | 428.15 | 0.86 LC-1 |
| 19 method B | (3S)-2-(3-(benzo[d]oxazol-2-yl(methyl)amino)-6-fluoro-3,4-dihydro-1H-carbazol-9(2H)-yl)acetic acid | 394.20 | 0.70 LC-1 |
| 20 method B | (3S)-2-(3-(benzo[d]thiazol-2-yl(methyl)amino)-6-fluoro-3,4-dihydro-1H-carbazol-9(2H)-yl)acetic acid | 410.19 | 0.68 LC-1 |
| 21 method B | (3S)-2-(6-fluoro-3-(methyl(quinazolin-4-yl)amino)-3,4-dihydro-1H-carbazol-9(2H)-yl)acetic acid | 405.16 | 0.55 LC-1 |
| 22 method B | (3S)-2-(6-fluoro-3-(methyl(2-(trifluoromethyl)quinazolin-4-yl)amino)-3,4-dihydro-1H-carbazol-9(2H)-yl)acetic acid | 473.16 | 0.86 LC-1 |
| 23 method B | (3S)-2-(6-fluoro-3-(methyl(2-methylquinazolin-4-yl)amino)-3,4-dihydro-1H-carbazol-9(2H)-yl)acetic acid | 419.24 | 0.58 LC-1 |
| 24 method B | (3S)-2-(3-((5-chloropyrimidin-2-yl)(ethyl)amino)-6-fluoro-3,4-dihydro-1H-carbazol-9(2H)-yl)acetic acid | 403.09 | 1.26 LC-1 |
| 25 method B | (3S)-2-(3-((5-chloropyrimidin-2-yl)(propyl)amino)-6-fluoro-3,4-dihydro-1H-carbazol-9(2H)-yl)acetic acid | 417.03 | 1.30 LC-1 |
| 26 method B | (3S)-2-(3-((5-chloropyrimidin-2-yl)(isopropyl)amino)-6-fluoro-3,4-dihydro-1H-carbazol-9(2H)-yl)acetic acid | 417.04 | 1.28 LC-1 |
| 27 method B | (3S)-2-(3-((5-chloropyrimidin-2-yl)(cyclopropylmethyl)amino)-6-fluoro-3,4-dihydro-1H-carbazol-9(2H)-yl)acetic acid | 429.17 | 1.30 LC-1 |
| 28 method B | (3S)-2-(6-fluoro-3-(methyl(quinazolin-2-yl)amino)-3,4-dihydro-1H-carbazol-9(2H)-yl)acetic acid | 405.12 | 0.72 LC-2 |
| 29 method B | (3S)-2-(6-fluoro-3-((5-fluorobenzo[d]oxazol-2-yl)(methyl)amino)-3,4-dihydro-1H-carbazol-9(2H)-yl)acetic acid | 412.09 | 0.88 LC-2 |
| 30 method B | (3S)-2-(6-fluoro-3-(methyl(5-phenylpyrimidin-2-yl)amino)-3,4-dihydro-1H-carbazol-9(2H)-yl)acetic acid | 431.02 | 0.91 LC-2 |
| 31 method B | (3S)-2-(6-fluoro-3-((5-methoxypyrimidin-2-yl)(methyl)amino)-3,4-dihydro-1H-carbazol-9(2H)-yl)acetic acid | 385.01 | 1.06 LC-1 |
| 32 method B | (3S)-2-(3-((6-chlorobenzo[d]thiazol-2-yl)(methyl)amino)-6-fluoro-3,4-dihydro-1H-carbazol-9(2H)-yl)acetic acid | 444.0 | 0.91 LC-2 |
| 33 method B | (3S)-2-(3-((5-chlorobenzo[d]thiazol-2-yl)(methyl)amino)-6-fluoro-3,4-dihydro-1H-carbazol-9(2H)-yl)acetic acid | 443.95 | 0.92 LC-2 |
| 34 method B | (3S)-2-(3-((5-chloropyrimidin-2-yl)(2-methoxyethyl)amino)-6-fluoro-3,4-dihydro-1H-carbazol-9(2H)-yl)acetic acid | 433.0 | 0.93 LC-2 |
| 35 method C | (3S)-2-(6-fluoro-3-(methyl(5-(trifluoromethyl)pyridin-2-yl)amino)-3,4-dihydro-1H-carbazol-9(2H)-yl)acetic acid | 422.12 | 0.87 LC-2 |
| 36 method C | (3S)-2-(6-fluoro-3-((5-fluoropyridin-2-yl)(methyl)amino)-3,4-dihydro-1H-carbazol-9(2H)-yl)acetic acid | 372.05 | 0.70 LC-2 |
| 37 method C | (3S)-2-(3-((5-chloropyridin-2-yl)(methyl)amino)-6-fluoro-3,4-dihydro-1H-carbazol-9(2H)-yl)acetic acid | 388.11 | 0.76 LC-2 |
| 38 method B | (3S)-2-(6-fluoro-3-((6-fluorobenzo[d]thiazol-2-yl)(methyl)amino)-3,4-dihydro-1H-carbazol-9(2H)-yl)acetic acid | 427.97 | 0.86 LC-2 |
| 39 method B | (3S)-2-(6-fluoro-3-((5-fluorobenzo[d]thiazol-2-yl)(methyl)amino)-3,4-dihydro-1H-carbazol-9(2H)-yl)acetic acid | 428.08 | 0.88 LC-2 |
| 40 method B | (3S)-2-(6-fluoro-3-((6-chlorobenzo[d]oxazol-2-yl)(methyl)amino)-3,4-dihydro-1H-carbazol-9(2H)-yl)acetic acid | 428.02 | 0.92 LC-2 |
| 41 method B | (3S)-2-(3-((5-chloropyrimidin-2-yl)(2,2-difluoroethyl)amino)-6-fluoro-3,4-dihydro-1H-carbazol-9(2H)-yl)acetic acid | 439.09 | 0.96 LC-2 |
| 42 method B | (3S)-2-(3-((5-cyclopropylpyrimidin-2-yl)(methyl)amino)-6-fluoro-3,4-dihydro-1H-carbazol-9(2H)-yl)acetic acid | 395.21 | 0.92 LC-2 |

TABLE 7-continued

| Example Method | Name | [M + H]⁺ m/z | $t_{R\,[min.]}$ LC-MS method |
|---|---|---|---|
| 43 method B | (3S)-2-(6-fluoro-3-((6-fluorobenzo[d]oxazol-2-yl)(methyl)amino)-3,4-dihydro-1H-carbazol-9(2H)-yl)acetic acid | 412.19 | 0.87 LC-2 |
| 44 method B | (3S)-2-(6-fluoro-3-(methyl(quinoxalin-2-yl)amino)-3,4-dihydro-1H-carbazol-9(2H)-yl)acetic acid | 405.09 | 0.72 LC-2 |
| 45 method B | 2-(6-fluoro-3-(methyl(4-methylthiazol-2-yl)amino)-3,4-dihydro-1H-carbazol-9(2H)-yl)acetic acid | 374.12 | 0.66 LC-2 |
| 46 method B | 2-(3-((4-(tert-butyl)thiazol-2-yl)(methyl)amino)-6-fluoro-3,4-dihydro-1H-carbazol-9(2H)-yl)acetic acid | 416.14 | 0.76 LC-2 |
| 47 method B | 2-(6-fluoro-3-(methyl(4-(trifluoromethyl)thiazol-2-yl)amino)-3,4-dihydro-1H-carbazol-9(2H)-yl)acetic acid | 428.07 | 0.94 LC-2 |
| 48 method B | 2-(3-((5-(tert-butyl)isoxazol-3-yl)(methyl)amino)-6-fluoro-3,4-dihydro-1H-carbazol-9(2H)-yl)acetic acid | 400.18 | 0.88 LC-2 |
| 49 method B | 2-(6-fluoro-3-(methyl(1-methyl-1H-pyrazol-3-yl)amino)-3,4-dihydro-1H-carbazol-9(2H)-yl)acetic acid | 357.2 | 0.67 LC-2 |
| 50 method B | 2-(6-fluoro-3-(methyl(5-methyl-1,3,4-thiadiazol-2-yl)amino)-3,4-dihydro-1H-carbazol-9(2H)-yl)acetic acid | 375.09 | 0.76 LC-2 |
| 51 method C | 2-(6-fluoro-3-(isoxazol-3-yl(methyl)amino)-3,4-dihydro-1H-carbazol-9(2H)-yl)acetic acid | 344.19 | 0.92 LC-2 |
| 52 method C | 2-(6-fluoro-3-(methyl(5-methylisoxazol-3-yl)amino)-3,4-dihydro-1H-carbazol-9(2H)-yl)acetic acid | 358.18 | 0.83 LC-2 |
| 53 method B | 2-(3-((5-chloropyrimidin-2-yl)(methyl)amino)-3,4-dihydro-1H-carbazol-9(2H)-yl)acetic acid | 371.07 | 0.91 LC-2 |
| 54 method B | 2-(6-chloro-3-((5-chloropyrimidin-2-yl)(methyl)amino)-3,4-dihydro-1H-carbazol-9(2H)-yl)acetic acid | 405.01 | 0.95 LC-2 |
| 55 method B | 2-(3-((5-chloropyrimidin-2-yl)(methyl)amino)-6-methyl-3,4-dihydro-1H-carbazol-9(2H)-yl)acetic acid | 385.01 | 0.94 LC-2 |
| 56 method B | 2-(3-((5-chloropyrimidin-2-yl)(methyl)amino)-6-(trifluoromethoxy)-3,4-dihydro-1H-carbazol-9(2H)-yl)acetic acid | 455.03 | 0.97 LC-2 |
| 57 method B | 2-(3-((5-chloropyrimidin-2-yl)(methyl)amino)-6-methoxy-3,4-dihydro-1H-carbazol-9(2H)-yl)acetic acid | 401.03 | 0.89 LC-2 |
| 58 method B | 2-(3-((5-chloropyrimidin-2-yl)(methyl)amino)-6-(trifluoromethyl)-3,4-dihydro-1H-carbazol-9(2H)-yl)acetic acid | 439.07 | 0.96 LC-2 |

Biological Assays:

Preparation of hCRTH2 Receptor Membranes and Radioligand Displacement Assay:

First, recombinant HEK293-hCRTH$_2$ cells were detached from culture plates into 5 ml buffer A/plate (Buffer A: 5 mM Tris, 1 mM MgCl$_2$-6H$_2$O pH=7.4) using a rubber policeman. Cells were then transferred into centrifugation tubes and centrifuged for 5 min at 400 g. The cell pellet was resuspended in the same buffer and tubes were frozen at −80° C. Cells were thawed and membrane fragments were generated by homogenization using a polytron homogenizer (30 seconds). The membrane fragments were then centrifuged at 3000 g for 20 minutes and resuspended in buffer C (Buffer C: 75 mM Tris, 25 mM MgCl$_2$, 250 mM Saccharose pH 7.4). Aliquots of membrane fragements were stored at −20° C.

Binding assay was performed in a final assay volume of 250 μl. First, 25 μl of test compound, previously diluted in Binding-Buffer (Binding-Buffer: 50 mM Tris-Base, 100 mM NaCl, 1 mM EDTA, 0.1% BSA (protease free), 0.01% NaN$_3$, 10 mM MnCl$_2$ pH 7.0) was placed into each well. After addition of 75 μl Binding-Buffer, 50 μl of the radioligand $^3$H-PGD$_2$ (at 2.5 nM (220.000 dpm/well) from ANAWA ART0662) was added to each well. Binding assay was started by addition of 100 μl CRTH$_2$ membrane fragments, reaching a final concentration of 20 μg/well. For non-specific binding, PGD$_2$ was added to the reaction mixture to 10 mM final concentration. This assay mix was incubated for 90 minutes at room temperature and then filtered through a GF/C filter 96-well plate which was pre-soaked for 3 hours in 0.5% polyethyleneimine (PEI). The filter-wells were washed three times with ice cold Binding-Buffer. Then, 40 μl of Microscint-40 (Packard) was added to each well and the retained radioactivity quantified in a Topcount (Packard).

Antagonistic activities of exemplified compounds are displayed in Table 8.

| Example | Name | IC$_{50}$ [nM] |
|---|---|---|
| 1 | (3S)-2-(6-fluoro-3-((5-fluoropyrimidin-2-yl)amino)-3,4-dihydro-1H-carbazol-9-(2H)-yl)acetic acid | 16 |
| 2 | (3R)-2-(6-fluoro-3-((5-fluoropyrimidin-2-yl)amino)-3,4-dihydro-1H-carbazol-9-(2H)-yl)acetic acid | 27 |

-continued

| Example | Name | IC$_{50}$ [nM] |
|---|---|---|
| 3 | (3S)-2-(6-fluoro-3-((5-chloropyrimidin-2-yl)amino)-3,4-dihydro-1H-carbazol-9-(2H)-yl)acetic acid | 4.6 |
| 4 | (3R)-2-(6-fluoro-3-((5-chloropyrimidin-2-yl)amino)-3,4-dihydro-1H-carbazol-9-(2H)-yl)acetic acid | 13 |
| 5 | (3R)-2-(6-fluoro-3-((5-(trifluoromethyl)pyrimidin-2-yl)amino)-3,4-dihydro-1H-carbazol-9-(2H)-yl)acetic acid | 27 |
| 6 | (3R)-2-(6-fluoro-3-((4-(trifluoromethyl)pyrimidin-2-yl)amino)-3,4-dihydro-1H-carbazol-9-(2H)-yl)acetic acid | 46 |
| 7 | (3S)-2-(6-fluoro-3-((5-fluoropyrimidin-2-yl)(methyl)amino)-3,4-dihydro-1H-carbazol-9(2H)-yl)acetic acid | 2.5 |
| 8 | (3R)-2-(6-fluoro-3-((5-fluoropyrimidin-2-yl)(methyl)amino)-3,4-dihydro-1H-carbazol-9(2H)-yl)acetic acid | 42 |
| 9 | (3S)-2-(3-((5-chloropyrimidin-2-yl)(methyl)amino)-6-fluoro-3,4-dihydro-1H-carbazol-9(2H)-yl)acetic acid | 2.7 |
| 10 | (3R)-2-(3-((5-chloropyrimidin-2-yl)(methyl)amino)-6-fluoro-3,4-dihydro-1H-carbazol-9(2H)-yl)acetic acid | 58 |
| 11 | (3S)-2-(6-fluoro-3-(methyl(5-(trifluoromethyl)pyrimidin-2-yl)amino)-3,4-dihydro-1H-carbazol-9(2H)-yl)acetic acid | 2.0 |
| 12 | (3R)-2-(6-fluoro-3-(methyl(5-(trifluoromethyl)pyrimidin-2-yl)amino)-3,4-dihydro-1H-carbazol-9(2H)-yl)acetic acid | 141 |
| 13 | (3S)-2-(6-fluoro-3-(methyl(4-(trifluoromethyl)pyrimidin-2-yl)amino)-3,4-dihydro-1H-carbazol-9(2H)-yl)acetic acid | 12 |
| 14 | (3R)-2-(6-fluoro-3-(methyl(4-(trifluoromethyl)pyrimidin-2-yl)amino)-3,4-dihydro-1H-carbazol-9(2H)-yl)acetic acid | 67 |
| 15 | (3S)-2-(6-fluoro-3-(methyl(pyrimidin-2-yl)amino)-3,4-dihydro-1H-carbazol-9(2H)-yl)acetic acid | 9.9 |
| 16 | (3S)-2-(3-((4,6-dimethylpyrimidin-2-yl)(methyl)amino)-6-fluoro-3,4-dihydro-1H-carbazol-9(2H)-yl)acetic acid | 125 |
| 17 | (3S)-2-(6-fluoro-3-(methyl(4-methylpyrimidin-2-yl)amino)-3,4-dihydro-1H-carbazol-9(2H)-yl)acetic acid | 107 |
| 18 | (3S)-2-(3-((5-chlorobenzo[d]oxazol-2-yl)(methyl)amino)-6-fluoro-3,4-dihydro-1H-carbazol-9(2H)-yl)acetic acid | 1.4 |
| 19 | (3S)-2-(3-(benzo[d]oxazol-2-yl(methyl)amino)-6-fluoro-3,4-dihydro-1H-carbazol-9(2H)-yl)acetic acid | 7.3 |
| 20 | (3S)-2-(3-(benzo[d]thiazol-2-yl(methyl)amino)-6-fluoro-3,4-dihydro-1H-carbazol-9(2H)-yl)acetic acid | 8.1 |
| 21 | (3S)-2-(6-fluoro-3-(methyl(quinazolin-4-yl)amino)-3,4-dihydro-1H-carbazol-9(2H)-yl)acetic acid | 26 |
| 22 | (3S)-2-(6-fluoro-3-(methyl(2-(trifluoromethyl)quinazolin-4-yl)amino)-3,4-dihydro-1H-carbazol-9(2H)-yl)acetic acid | 16 |
| 23 | (3S)-2-(6-fluoro-3-(methyl(2-methylquinazolin-4-yl)amino)-3,4-dihydro-1H-carbazol-9(2H)-yl)acetic acid | 55 |
| 24 | (3S)-2-(3-((5-chloropyrimidin-2-yl)(ethyl)amino)-6-fluoro-3,4-dihydro-1H-carbazol-9(2H)-yl)acetic acid | 1.7 |
| 25 | (3S)-2-(3-((5-chloropyrimidin-2-yl)(propyl)amino)-6-fluoro-3,4-dihydro-1H-carbazol-9(2H)-yl)acetic acid | 3.9 |
| 26 | (3S)-2-(3-((5-chloropyrimidin-2-yl)(isopropyl)amino)-6-fluoro-3,4-dihydro-1H-carbazol-9(2H)-yl)acetic acid | 809 |
| 27 | (3S)-2-(3-((5-chloropyrimidin-2-yl)(cyclopropylmethyl)amino)-6-fluoro-3,4-dihydro-1H-carbazol-9(2H)-yl)acetic acid | 1.7 |
| 28 | (3S)-2-(6-fluoro-3-(methyl(quinazolin-2-yl)amino)-3,4-dihydro-1H-carbazol-9(2H)-yl)acetic acid | 12 |
| 29 | (3S)-2-(6-fluoro-3-((5-fluorobenzo[d]oxazol-2-yl)(methyl)amino)-3,4-dihydro-1H-carbazol-9(2H)-yl)acetic acid | 4.1 |
| 30 | (3S)-2-(6-fluoro-3-(methyl(5-phenylpyrimidin-2-yl)amino)-3,4-dihydro-1H-carbazol-9(2H)-yl)acetic acid | 11 |
| 31 | (3S)-2-(6-fluoro-3-((5-methoxypyrimidin-2-yl)(methyl)amino)-3,4-dihydro-1H-carbazol-9(2H)-yl)acetic acid | 7.2 |
| 32 | (3S)-2-(3-((6-chlorobenzo[d]thiazol-2-yl)(methyl)amino)-6-fluoro-3,4-dihydro-1H-carbazol-9(2H)-yl)acetic acid | 6.7 |
| 33 | (3S)-2-(3-((5-chlorobenzo[d]thiazol-2-yl)(methyl)amino)-6-fluoro-3,4-dihydro-1H-carbazol-9(2H)-yl)acetic acid | 10 |
| 34 | (3S)-2-(3-((5-chloropyrimidin-2-yl)(2-methoxyethyl)amino)-6-fluoro-3,4-dihydro-1H-carbazol-9(2H)-yl)acetic acid | 5.9 |
| 35 | (3S)-2-(6-fluoro-3-(methyl(5-(trifluoromethyl)pyridin-2-yl)amino)-3,4-dihydro-1H-carbazol-9(2H)-yl)acetic acid | 9.1 |
| 36 | (3S)-2-(6-fluoro-3-((5-fluoropyridin-2-yl)(methyl)amino)-3,4-dihydro-1H-carbazol-9(2H)-yl)acetic acid | 9.8 |
| 37 | (3S)-2-(3-((5-chloropyridin-2-yl)(methyl)amino)-6-fluoro-3,4-dihydro-1H-carbazol-9(2H)-yl)acetic acid | 5.2 |
| 38 | (3S)-2-(6-fluoro-3-((6-fluorobenzo[d]thiazol-2-yl)(methyl)amino)-3,4-dihydro-1H-carbazol-9(2H)-yl)acetic acid | 1.2 |
| 39 | (3S)-2-(6-fluoro-3-((5-fluorobenzo[d]thiazol-2-yl)(methyl)amino)-3,4-dihydro-1H-carbazol-9(2H)-yl)acetic acid | 3.1 |
| 40 | (3S)-2-(6-fluoro-3-((6-chlorobenzo[d]oxazol-2-yl)(methyl)amino)-3,4-dihydro-1H-carbazol-9(2H)-yl)acetic acid | 2.0 |

-continued

| Example | Name | IC$_{50}$ [nM] |
|---|---|---|
| 41 | (3S)-2-(3-((5-chloropyrimidin-2-yl)(2,2-difluoroethyl)amino)-6-fluoro-3,4-dihydro-1H-carbazol-9(2H)-yl)acetic acid | 15 |
| 42 | (3S)-2-(3-((5-chloropyrimidin-2-yl)(methyl)amino)-6-fluoro-3,4-dihydro-1H-carbazol-9(2H)-yl)acetic acid | 2.2 |
| 43 | (3S)-2-(6-fluoro-3-((6-fluorobenzo[d]oxazol-2-yl)(methyl)amino)-3,4-dihydro-1H-carbazol-9(2H)-yl)acetic acid | 4.6 |
| 44 | (3S)-2-(6-fluoro-3-(methyl(quinoxalin-2-yl)amino)-3,4-dihydro-1H-carbazol-9(2H)-yl)acetic acid | 11 |
| 45 | 2-(6-fluoro-3-(methyl(4-methylthiazol-2-yl)amino)-3,4-dihydro-1H-carbazol-9(2H)-yl)acetic acid | 9.7 |
| 46 | 2-(3-((4-(tert-butyl)thiazol-2-yl)(methyl)amino)-6-fluoro-3,4-dihydro-1H-carbazol-9(2H)-yl)acetic acid | 73 |
| 47 | 2-(6-fluoro-3-(methyl(4-trifluoromethyl)thiazol-2-yl)amino)-3,4-dihydro-1H-carbazol-9(2H)-yl)acetic acid | 14 |
| 48 | 2-(3-((5-(tert-butyl)isoxazol-3-yl)(methyl)amino)-6-fluoro-3,4-dihydro-1H-carbazol-9(2H)-yl)acetic acid | 72 |
| 49 | 2-(6-fluoro-3-(methyl(1-methyl-1H-pyrazol-3-yl)amino)-3,4-dihydro-1H-carbazol-9(2H)-yl)acetic acid | 37 |
| 50 | 2-(6-fluoro-3-(methyl(5-methyl-1,3,4-thiadiazol-2-yl)amino)-3,4-dihydro-1H-carbazol-9(2H)-yl)acetic acid | 127 |
| 51 | 2-(6-fluoro-3-(isoxazol-3-yl(methyl)amino)-3,4-dihydro-1H-carbazol-9(2H)-yl)acetic acid | 6.4 |
| 52 | 2-(6-fluoro-3-(methyl(5-methylisoxazol-3-yl)amino)-3,4-dihydro-1H-carbazol-9(2H)-yl)acetic acid | 7.4 |
| 53 | 2-(3-((5-chloropyrimidin-2-yl)(methyl)amino)-3,4-dihydro-1H-carbazol-9(2H)-yl)acetic acid | 5.1 |
| 54 | 2-(6-chloro-3-((5-chloropyrimidin-2-yl)(methyl)amino)-3,4-dihydro-1H-carbazol-9(2H)-yl)acetic acid | 2.0 |
| 55 | 2-(3-((5-chloropyrimidin-2-yl)(methyl)amino)-6-methyl-3,4-dihydro-1H-carbazol-9(2H)-yl)acetic acid | 5.5 |
| 56 | 2-(3-((5-chloropyrimidin-2-yl)(methyl)amino)-6-(trifluoromethoxy)-3,4-dihydro-1H-carbazol-9(2H)-yl)acetic acid | 8.8 |
| 57 | 2-(3-((5-chloropyrimidin-2-yl)(methyl)amino)-6-methoxy-3,4-dihydro-1H-carbazol-9(2H)-yl)acetic acid | 4.6 |
| 58 | 2-(3-((5-chloropyrimidin-2-yl)(methyl)amino)-6-(trifluoromethyl)-3,4-dihydro-1H-carbazol-9(2H)-yl)acetic acid | 3.5 |

Radioligand Displacement Assay-Human Serum Albumin (HSA):

Radioligand displacement assay in presence of human serum albumin (HSA) was performed as described above, with following modifications. Binding-Buffer-HSA: Binding-buffer+0.5% Sigma Albumin from Human serum A1887 (instead of 0.1% BSA). A volume of 25 µl test compound, previously diluted in Binding-Buffer-HSA was placed into each well. After addition of 75 µl Binding-Buffer-HSA, 50 µl of $^3$H-PGD$_2$ (at 2.5 nM (220.000 dpm/well) from ANAWA ART0662) was added to each well. Remaining protocol was identical as described above.

Antagonistic activities of exemplified compounds are displayed in Table 9.

| Example | Name | IC$_{50}$ [nM] |
|---|---|---|
| 1 | (3S)-2-(6-fluoro-3-((5-fluoropyrimidin-2-yl)amino)-3,4-dihydro-1H-carbazol-9-(2H)-yl)acetic acid | 20 |
| 3 | (3S)-2-(6-fluoro-3-((5-chloropyrimidin-2-yl)amino)-3,4-dihydro-1H-carbazol-9-(2H)-yl)acetic acid | 23 |
| 4 | (3R)-2-(6-fluoro-3-((5-chloropyrimidin-2-yl)amino)-3,4-dihydro-1H-carbazol-9-(2H)-yl)acetic acid | 27 |
| 7 | (3S)-2-(6-fluoro-3-((5-fluoropyrimidin-2-yl)(methyl)amino)-3,4-dihydro-1H-carbazol-9(2H)-yl)acetic acid | 7 |
| 9 | (3S)-2-(3-((5-chloropyrimidin-2-yl)(methyl)amino)-6-fluoro-3,4-dihydro-1H-carbazol-9(2H)-yl)acetic acid | 11 |
| 11 | (3S)-2-(6-fluoro-3-(methyl(5-(trifluoromethyl)pyrimidin-2-yl)amino)-3,4-dihydro-1H-carbazol-9(2H)-yl)acetic acid | 15 |
| 13 | (3S)-2-(6-fluoro-3-(methyl(4-(trifluoromethyl)pyrimidin-2-yl)amino)-3,4-dihydro-1H-carbazol-9(2H)-yl)acetic acid | 769 |
| 15 | (3S)-2-(6-fluoro-3-(methyl(pyrimidin-2-yl)amino)-3,4-dihydro-1H-carbazol-9(2H)-yl)acetic acid | 35 |
| 18 | (3S)-2-(3-((5-chlorobenzo[d]oxazol-2-yl)(methyl)amino)-6-fluoro-3,4-dihydro-1H-carbazol-9(2H)-yl)acetic acid | 28 |
| 19 | (3S)-2-(3-(benzo[d]oxazol-2-yl(methyl)amino)-6-fluoro-3,4-dihydro-1H-carbazol-9(2H)-yl)acetic acid | 17 |
| 20 | (3S)-2-(3-(benzo[d]thiazol-2-yl(methyl)amino)-6-fluoro-3,4-dihydro-1H-carbazol-9(2H)-yl)acetic acid | 40 |

| Example | Name | IC$_{50}$ [nM] |
|---|---|---|
| 22 | (3S)-2-(6-fluoro-3-(methyl(2-(trifluoromethyl)quinazolin-4-yl)amino)-3,4-dihydro-1H-carbazol-9(2H)-yl)acetic acid | 380 |
| 24 | (3S)-2-(3-((5-chloropyrimidin-2-yl)(ethyl)amino)-6-fluoro-3,4-dihydro-1H-carbazol-9(2H)-yl)acetic acid | 19 |
| 25 | (3S)-2-(3-((5-chloropyrimidin-2-yl)(propyl)amino)-6-fluoro-3,4-dihydro-1H-carbazol-9(2H)-yl)acetic acid | 17 |
| 27 | (3S)-2-(3-((5-chloropyrimidin-2-yl)(cyclopropylmethyl)amino)-6-fluoro-3,4-dihydro-1H-carbazol-9(2H)-yl)acetic acid | 6 |
| 28 | (3S)-2-(6-fluoro-3-(methyl(quinazolin-2-yl)amino)-3,4-dihydro-1H-carbazol-9(2H)-yl)acetic acid | 22 |
| 29 | (3S)-2-(6-fluoro-3-((5-fluorobenzo[d]oxazol-2-yl)(methyl)amino)-3,4-dihydro-1H-carbazol-9(2H)-yl)acetic acid | 7 |
| 30 | (3S)-2-(6-fluoro-3-(methyl(5-phenylpyrimidin-2-yl)amino)-3,4-dihydro-1H-carbazol-9(2H)-yl)acetic acid | 41 |
| 31 | (3S)-2-(6-fluoro-3-((5-methoxypyrimidin-2-yl)(methyl)amino)-3,4-dihydro-1H-carbazol-9(2H)-yl)acetic acid | 43 |
| 32 | (3S)-2-(3-((6-chlorobenzo[d]thiazol-2-yl)(methyl)amino)-6-fluoro-3,4-dihydro-1H-carbazol-9(2H)-yl)acetic acid | 20 |
| 33 | (3S)-2-(3-((5-chlorobenzo[d]thiazol-2-yl)(methyl)amino)-6-fluoro-3,4-dihydro-1H-carbazol-9(2H)-yl)acetic acid | 8 |
| 34 | (3S)-2-(3-((5-chloropyrimidin-2-yl)(2-methoxyethyl)amino)-6-fluoro-3,4-dihydro-1H-carbazol-9(2H)-yl)acetic acid | 14 |
| 35 | (3S)-2-(6-fluoro-3-(methyl(5-(trifluoromethyl)pyridin-2-yl)amino)-3,4-dihydro-1H-carbazol-9(2H)-yl)acetic acid | 20 |
| 36 | (3S)-2-(6-fluoro-3-((5-fluoropyridin-2-yl)(methyl)amino)-3,4-dihydro-1H-carbazol-9(2H)-yl)acetic acid | 8 |
| 37 | (3S)-2-(3-((5-chloropyridin-2-yl)(methyl)amino)-6-fluoro-3,4-dihydro-1H-carbazol-9(2H)-yl)acetic acid | 13 |
| 38 | (3S)-2-(6-fluoro-3-((6-fluorobenzo[d]thiazol-2-yl)(methyl)amino)-3,4-dihydro-1H-carbazol-9(2H)-yl)acetic acid | 9 |
| 39 | (3S)-2-(6-fluoro-3-((5-fluorobenzo[d]thiazol-2-yl)(methyl)amino)-3,4-dihydro-1H-carbazol-9(2H)-yl)acetic acid | 6 |
| 40 | (3S)-2-(6-fluoro-3-(((6-chlorobenzo[d]oxazol-2-yl)methyl)amino)-3,4-dihydro-1H-carbazol-9(2H)-yl)acetic acid | 21 |
| 41 | (3S)-2-(3-((5-chloropyrimidin-2-yl)(2,2-difluoroethyl)amino)-6-fluoro-3,4-dihydro-1H-carbazol-9(2H)-yl)acetic acid | 68 |
| 42 | (3S)-2-(3-(((5-cyclopropylpyrimidin-2-yl)methyl)amino)-6-fluoro-3,4-dihydro-1H-carbazol-9(2H)-yl)acetic acid | 36 |
| 43 | (3S)-2-(6-fluoro-3-((6-fluorobenzo[d]oxazol-2-yl)(methyl)amino)-3,4-dihydro-1H-carbazol-9(2H)-yl)acetic acid | 12 |
| 44 | (3S)-2-(6-fluoro-3-(methyl(quinoxalin-2-yl)amino)-3,4-dihydro-1H-carbazol-9(2H)-yl)acetic acid | 176 |
| 45 | 2-(6-fluoro-3-(methyl(4-methylthiazol-2-yl)amino)-3,4-dihydro-1H-carbazol-9(2H)-yl)acetic acid | 25 |
| 47 | 2-(6-fluoro-3-(methyl(4-(trifluoromethyl)thiazol-2-yl)amino)-3,4-dihydro-1H-carbazol-9(2H)-yl)acetic acid | 402 |
| 51 | 2-(6-fluoro-3-(isoxazol-3-yl(methyl)amino)-3,4-dihydro-1H-carbazol-9(2H)-yl)acetic acid | 53 |
| 52 | 2-(6-fluoro-3-(methyl(5-methylisoxazol-3-yl)amino)-3,4-dihydro-1H-carbazol-9(2H)-yl)acetic acid | 58 |
| 53 | 2-(3-((5-chloropyrimidin-2-yl)(methyl)amino)-3,4-dihydro-1H-carbazol-9(2H)-yl)acetic acid | 16 |
| 54 | 2-(6-chloro-3-((5-chloropyrimidin-2-yl)(methyl)amino)-3,4-dihydro-1H-carbazol-9(2H)-yl)acetic acid | 3 |
| 55 | 2-(3-((5-chloropyrimidin-2-yl)(methyl)amino)-6-methyl-3,4-dihydro-1H-carbazol-9(2H)-yl)acetic acid | 40 |
| 56 | 2-(3-((5-chloropyrimidin-2-yl)(methyl)amino)-6-(trifluoromethoxy)-3,4-dihydro-1H-carbazol-9(2H)-yl)acetic acid | 303 |
| 57 | 2-(3-((5-chloropyrimidin-2-yl)(methyl)amino)-6-methoxy-3,4-dihydro-1H-carbazol-9(2H)-yl)acetic acid | 56 |
| 58 | 2-(3-((5-chloropyrimidin-2-yl)(methyl)amino)-6-(trifluoromethyl)-3,4-dihydro-1H-carbazol-9(2H)-yl)acetic acid | 15 |

REFERENCES

Shimizu T, Yamashita A, Hayaishi O, Specific binding of prostaglandin D2 to rat brain synaptic membranes. J. Biol. Chem. 1982. Vol. 257:13570-13575.

Fortini A, Modesti P A, Abbate R, Gensini G F, Neri Serneri G G. Heparin does not interfere with prostacyclin and prostaglandin D2 binding to platelets. Thromb. Res. 1985. Vol. 40:319-328.

Sawyer N, Cauchon E, Chateauneuf A, Cruz R P, Nicholson D W, Metters K M, O'Neill G P, Gervais F G. Molecular pharmacology of the human PGD2 receptor CRTH2. Br. J. of Pharmacol. 2002. Vol. 137:1163-1172

Eosinophil Shape Change Assay with Human Plasma

After obtaining informed consent, blood samples were drawn by venipuncture according to the protocol approved by the ethics committee of Basel, Switzerland. Polymorphonuclear leukocytes (containing eosinophils, basophils and neutrophils) were isolated using the Polymorphprep™ method (Axis-Shield). In brief, anticoagulated whole blood was layered onto a Polymorphprep gradient (density 1.113 g/ml) and centrifuged at 500 g for 30 min. The polymorphonuclear cell fraction was harvested and depleted for erythrocytes by hypotonic saline lysis.

The polymorphonuclear cells were resuspended in assay buffer (1×PBS with $Ca^{2+}/Mg^{2+}$ supplemented with 0.1% BSA, 10 mM HEPES, and 10 mM Glucose, pH 7.4) at $5 \times 10^6$ cells/ml and stained with anti-CD49d-APC ((APC=Allophycocyanin) for 1 hour at RT. Test compounds, at various concentrations, were preincubated 10 min in human plasma (anticoagulated with a thrombin inhibitor). Then, human plasma was added to the polymorphonuclear cells to 50% of final assay volume with polymorphonuclear cells at $4 \times 10^6$ cells/rd. After incubation for 10 minutes at 37° C., the polymorphonuclear cells were activated for 5 min at 37° C. by addition of $PGD_2$ at 100 nM final concentration. Activation was stopped by addition of 0.5 ml paraformaldehyde (1%).

Immediately after fixation with paraformaldehyde, the samples were analyzed by FACSCanto flow cytometer (BD Biosciences) and target cells were identified by their forward-scatter (FSC) and side-scatter (SSC) characteristics. Eosinophils were identified by the anti-CD49d-APC signal and their characteristic side-scatter (SSC) profile. Shape change responses, indicative of eosinophil activation, were quantified as the percent of cells with an increased forward-scatter.

Antagonistic activities of exemplified compounds are displayed in Table 10.

| Example | Name | $IC_{50}$ [nM] |
|---|---|---|
| 1 | (3S)-2-(6-fluoro-3-((5-fluoropyrimidin-2-yl)amino)-3,4-dihydro-1H-carbazol-9-(2H)-yl)acetic acid | 21 |
| 3 | (3S)-2-(6-fluoro-3-((5-chloropyrimidin-2-yl)amino)-3,4-dihydro-1H-carbazol-9-(2H)-yl)acetic acid | 41 |
| 4 | (3R)-2-(6-fluoro-3-((5-chloropyrimidin-2-yl)amino)-3,4-dihydro-1H-carbazol-9-(2H)-yl)acetic acid | 722 |
| 7 | (3S)-2-(6-fluoro-3-((5-fluoropyrimidin-2-yl)(methyl)amino)-3,4-dihydro-1H-carbazol-9(2H)-yl)acetic acid | 8 |
| 9 | (3S)-2-(3-((5-chloropyrimidin-2-yl)(methyl)amino)-6-fluoro-3,4-dihydro-1H-carbazol-9(2H)-yl)acetic acid | 15 |
| 11 | (3S)-2-(6-fluoro-3-(methyl(5-(trifluoromethyl)pyrimidin-2-yl)amino)-3,4-dihydro-1H-carbazol-9(2H)-yl)acetic acid | 49 |
| 15 | (3S)-2-(6-fluoro-3-(methyl(pyrimidin-2-yl)amino)-3,4-dihydro-1H-carbazol-9(2H)-yl)acetic acid | 66 |
| 18 | (3S)-2-(3-((5-chlorobenzo[d]oxazol-2-yl)(methyl)amino)-6-fluoro-3,4-dihydro-1H-carbazol-9(2H)-yl)acetic acid | 6 |
| 19 | (3S)-2-(3-(benzo[d]oxazol-2-yl(methyl)amino)-6-fluoro-3,4-dihydro-1H-carbazol-9(2H)-yl)acetic acid | 31 |
| 24 | (3S)-2-(3-((5-chloropyrimidin-2-yl)(ethyl)amino)-6-fluoro-3,4-dihydro-1H-carbazol-9(2H)-yl)acetic acid | 37 |
| 25 | (3S)-2-(3-((5-chloropyrimidin-2-yl)(propyl)amino)-6-fluoro-3,4-dihydro-1H-carbazol-9(2H)-yl)acetic acid | 13 |
| 27 | (3S)-2-(3-((5-chloropyrimidin-2-yl)(cyclopropylmethyl)amino)-6-fluoro-3,4-dihydro-1H-carbazol-9(2H)-yl)acetic acid | 14 |
| 28 | (3S)-2-(6-fluoro-3-(methyl(quinazolin-2-yl)amino)-3,4-dihydro-1H-carbazol-9(2H)-yl)acetic acid | 25 |
| 29 | (3S)-2-(6-fluoro-3-((5-fluorobenzo[d]oxazol-2-yl)(methyl)amino)-3,4-dihydro-1H-carbazol-9(2H)-yl)acetic acid | 4 |
| 32 | (3S)-2-(3-((6-chlorobenzo[d]thiazol-2-yl)(methyl)amino)-6-fluoro-3,4-dihydro-1H-carbazol-9(2H)-yl)acetic acid | 33 |
| 33 | (3S)-2-(3-((5-chlorobenzo[d]thiazol-2-yl)(methyl)amino)-6-fluoro-3,4-dihydro-1H-carbazol-9(2H)-yl)acetic acid | 46 |
| 34 | (3S)-2-(3-((5-chloropyrimidin-2-yl)(2-methoxyethyl)amino)-6-fluoro-3,4-dihydro-1H-carbazol-9(2H)-yl)acetic acid | 8 |
| 38 | (3S)-2-(6-fluoro-3-((6-fluorobenzo[d]thiazol-2-yl)(methyl)amino)-3,4-dihydro-1H-carbazol-9(2H)-yl)acetic acid | 2 |
| 39 | (3S)-2-(6-fluoro-3-((5-fluorobenzo[d]thiazol-2-yl)(methyl)amino)-3,4-dihydro-1H-carbazol-9(2H)-yl)acetic acid | 16 |
| 40 | (3S)-2-(6-fluoro-3-((6-chlorobenzo[d]oxazol-2-yl)(methyl)amino)-3,4-dihydro-1H-carbazol-9(2H)-yl)acetic acid | 75 |
| 42 | (3S)-2-(3-((5-cyclopropylpyrimidin-2-yl)(methyl)amino)-6-fluoro-3,4-dihydro-1H-carbazol-9(2H)-yl)acetic acid | 19 |
| 43 | (3S)-2-(6-fluoro-3-((6-fluorobenzo[d]oxazol-2-yl)(methyl)amino)-3,4-dihydro-1H-carbazol-9(2H)-yl)acetic acid | 6 |
| 45 | 2-(6-fluoro-3-(methyl(4-methylthiazol-2-yl)amino)-3,4-dihydro-1H-carbazol-9(2H)-yl)acetic acid | 414 |

Intracellular Calcium Mobilization Assay (FLIPR):

Cells (HEK-293), stably expressing the hCRTH2 receptor under the control of the cytomegalovirus promotor from a single insertion of the expression vector pcDNA5 (Invitrogen), are grown to confluency in DMEM (low glucose, Gibco) medium supplemented with 10% fetal calf serum (Bioconcept, Switzerland) under standard mammalian cell culture conditions (37° C. in a humidified atmosphere of 5% $CO_2$). Cells are detached from culture dishes using a dissociation buffer (0.02% EDTA in PBS, Gibco) for 1 min, and collected by centrifugation at 200 g at rt for 5 min in assay buffer (equal parts of Hank's BSS (HBSS, Bioconcept) and DMEM (low glucose, without phenol red, Gibco)). After incubation for 45 min (37° C. and 5% $CO_2$) in the presence of 1 μM Fluo-4 and 0.04% Pluronic F-127 (both Molecular Probes), and 20 mM HEPES (Gibco) in assay buffer, the cells are washed with and resuspended in assay buffer, then seeded onto 384-well FLIPR assay plates (Greiner) at 50,000 cells in 66 μl per well, and sedimented by centrifugation.

Stock solutions of test compounds are made up at a concentration of 10 mM in DMSO, and serially diluted in assay buffer to concentrations required for inhibition dose response curves. Prostaglandin $D_2$ (Biomol, Plymouth Meeting, Pa.) is used as an agonist.

A FLIPR Tetra instrument (Molecular Devices) is operated according to the manufacturers standard instructions, adding 4 µl of test compound dissolved at 10 mM in DMSO and diluted prior to the experiment in assay buffer to obtain the desired final concentration. 10 µl of 80 nM prostaglandin $D_2$ (Biomol, Plymouth Meeting, Pa.) in assay buffer, supplemented with 0.8% bovine serum albumin (fatty acid content <0.02%, Sigma), is then added to obtain a final concentration of 10 nM and 0.1%, respectively. Changes in fluorescence are monitored before and after the addition of test compounds at $\lambda_{ex}$=488 nm and $\lambda_{em}$=540 nm. Emission peak values above base level after prostaglandin $D_2$ addition are exported after base line subtraction. Values are normalized to high-level control (no test compound added) after subtraction of base line value (no prostaglandin $D_2$ added). The program XLlfit 3.0 (IDBS) is used to fit the data to a single site dose response curve of the equation $(A+((B-A)/(1+((C/x)^D))))$ and to calculate the $IC_{50}$ values.

The invention claimed is:

1. A compound of formula (I):

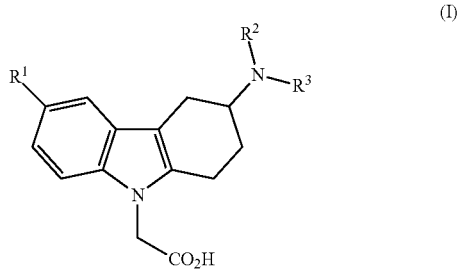

wherein
$R^1$ represents hydrogen, $(C_1$-$C_4)$alkyl, $(C_1$-$C_4)$alkoxy, halogen, trifluoromethoxy or trifluoromethyl;
$R^2$ represents hydrogen, $(C_1$-$C_4)$alkyl, $(C_1$-$C_2)$alkoxy-$(C_2$-$C_3)$alkyl, $(C_1$-$C_4)$fluoroalkyl or $(C_3$-$C_6)$cycloalkyl-$(C_1$-$C_2)$alkyl; and
$R^3$ represents a heteroaryl group which is unsubstituted or mono-, di- or tri-substituted, wherein the substituents are halogen, $(C_1$-$C_4)$alkyl, $(C_3$-$C_6)$cycloalkyl, $(C_1$-$C_4)$alkoxy, $(C_1$-$C_4)$fluoroalkyl and or phenyl;

or a salt of such a compound.

2. The compound according to claim 1, wherein
$R^1$ represents fluorine, chlorine or trifluoromethyl;
$R^2$ represents hydrogen, methyl, 2-methoxy-ethyl or cyclopropyl-methyl; and
$R^3$ represents a heteroaryl group which is mono-substituted with fluorine or chlorine;
or a salt of such a compound.

3. The compound according to claim 1, wherein
$R^1$ represents fluorine;
$R^2$ represents hydrogen or methyl; and
$R^3$ represents a heteroaryl group which is unsubstituted or mono-substituted with fluorine, chlorine or trifluoromethyl;
or a salt of such a compound.

4. The compound according to claim 1, wherein $R^1$ represents halogen;
or a salt of such a compound.

5. The compound according to claim 1, wherein $R^2$ represents hydrogen, methyl, ethyl, n-propyl, 2-methoxy-ethyl, 2,2-difluoroethyl or cyclopropyl-methyl;
or a salt of such a compound.

6. The compound according to claim 1, wherein $R^2$ represents methyl;
or a salt of such a compound.

7. The compound according to claim 1, wherein $R^3$ represents a heteroaryl group which is unsubstituted or monosubstituted with halogen, methoxy, trifluoromethyl or phenyl;
or a salt of such a compound.

8. The compound according to claim 1,
wherein $R^3$ represents a heteroaryl group which is unsubstituted or mono-substituted with fluorine, chlorine or trifluoromethyl,
wherein the heteroaryl is pyrimidyl, benzoxazolyl or benzothiazolyl;
or a salt of such a compound.

9. The compound according to claim 1, selected from:
(3S)-2-(6-fluoro-3-((5-fluoropyrimidin-2-yl)amino)-3,4-dihydro-1H-carbazol-9-(2H)-yl)acetic acid;
(3R)-2-(6-fluoro-3-((5-fluoropyrimidin-2-yl)amino)-3,4-dihydro-1H-carbazol-9-(2H)-yl)acetic acid;
(3S)-2-(6-fluoro-3-((5-chloropyrimidin-2-yl)amino)-3,4-dihydro-1H-carbazol-9-(2H)-yl)acetic acid;
(3R)-2-(6-fluoro-3-((5-chloropyrimidin-2-yl)amino)-3,4-dihydro-1H-carbazol-9-(2H)-yl)acetic acid;
(3R)-2-(6-fluoro-3-((5-(trifluoromethyl)pyrimidin-2-yl)amino)-3,4-dihydro-1H-carbazol-9-(2H)-yl)acetic acid;
(3R)-2-(6-fluoro-3-((4-(trifluoromethyl)pyrimidin-2-yl)amino)-3,4-dihydro-1H-carbazol-9-(2H)-yl)acetic acid;
(3S)-2-(6-fluoro-3-((5-fluoropyrimidin-2-yl)(methyl)amino)-3,4-dihydro-1H-carbazol-9(2H)-yl)acetic acid;
(3R)-2-(6-fluoro-3-((5-fluoropyrimidin-2-yl)(methyl)amino)-3,4-dihydro-1H-carbazol-9(2H)-yl)acetic acid;
(3S)-2-(3-((5-chloropyrimidin-2-yl)(methyl)amino)-6-fluoro-3,4-dihydro-1H-carbazol-9(2H)-yl)acetic acid;
(3R)-2-(3-((5-chloropyrimidin-2-yl)(methyl)amino)-6-fluoro-3,4-dihydro-1H-carbazol-9(2H)-yl)acetic acid;
(3S)-2-(6-fluoro-3-(methyl(5-(trifluoromethyl)pyrimidin-2-yl)amino)-3,4-dihydro-1H-carbazol-9(2H)-yl)acetic acid;
(3R)-2-(6-fluoro-3-(methyl(5-(trifluoromethyl)pyrimidin-2-yl)amino)-3,4-dihydro-1H-carbazol-9(2H)-yl) acetic acid;
(3S)-2-(6-fluoro-3-(methyl(4-(trifluoromethyl)pyrimidin-2-yl)amino)-3,4-dihydro-1H-carbazol-9(2H)-yl)acetic acid;
(3R)-2-(6-fluoro-3-(methyl(4-(trifluoromethyl)pyrimidin-2-yl)amino)-3,4-dihydro-1H-carbazol-9(2H)-yl) acetic acid;
(3S)-2-(6-fluoro-3-(methyl(pyrimidin-2-yl)amino)-3,4-dihydro-1H-carbazol-9(2H)-yl)acetic acid;
(3S)-2-(3-((4,6-dimethylpyrimidin-2-yl)(methyl)amino)-6-fluoro-3,4-dihydro-1H-carbazol-9(2H)-yl)acetic acid;
(3S)-2-(6-fluoro-3-(methyl(4-methylpyrimidin-2-yl)amino)-3,4-dihydro-1H-carbazol-9(2H)-yl)acetic acid;
(3S)-2-(3-((5-chlorobenzo[d]oxazol-2-yl)(methyl)amino)-6-fluoro-3,4-dihydro-1H-carbazol-9(2H)-yl) acetic acid;
(3S)-2-(3-(benzo[d]oxazol-2-yl(methyl)amino)-6-fluoro-3,4-dihydro-1H-carbazol-9(2H)-yl)acetic acid;
(3S)-2-(3-(benzo[d]thiazol-2-yl(methyl)amino)-6-fluoro-3,4-dihydro-1H-carbazol-9(2H)-yl)acetic acid;

(3S)-2-(6-fluoro-3-(methyl(quinazolin-4-yl)amino)-3,4-dihydro-1H-carbazol-9(2H)-yl)acetic acid;
(3S)-2-(6-fluoro-3-(methyl(2-(trifluoromethyl)quinazolin-4-yl)amino)-3,4-dihydro-1H-carbazol-9(2H)-yl) acetic acid;
(3S)-2-(6-fluoro-3-(methyl(2-methylquinazolin-4-yl)amino)-3,4-dihydro-1H-carbazol-9(2H)-yl)acetic acid;
(3S)-2-(3-((5-chloropyrimidin-2-yl)(ethyl)amino)-6-fluoro-3,4-dihydro-1H-carbazol-9(2H)-yl)acetic acid;
(3S)-2-(3-((5-chloropyrimidin-2-yl)(propyl)amino)-6-fluoro-3,4-dihydro-1H-carbazol-9(2H)-yl)acetic acid;
(3S)-2-(3-((5-chloropyrimidin-2-yl)(isopropyl)amino)-6-fluoro-3,4-dihydro-1H-carbazol-9(2H)-yl)acetic acid;
(3S)-2-(3-((5-chloropyrimidin-2-yl)(cyclopropylmethyl)amino)-6-fluoro-3,4-dihydro-1H-carbazol-9(2H)-yl) acetic acid;
(3S)-2-(6-fluoro-3-(methyl(quinazolin-2-yl)amino)-3,4-dihydro-1H-carbazol-9(2H)-yl)acetic acid;
(3S)-2-(6-fluoro-3-((5-fluorobenzo[d]oxazol-2-yl)(methyl)amino)-3,4-dihydro-1H-carbazol-9(2H)-yl)acetic acid;
(3S)-2-(6-fluoro-3-(methyl(5-phenylpyrimidin-2-yl)amino)-3,4-dihydro-1H-carbazol-9(2H)-yl)acetic acid;
(3S)-2-(6-fluoro-3-((5-methoxypyrimidin-2-yl)(methyl)amino)-3,4-dihydro-1H-carbazol-9(2H)-yl)acetic acid;
(3S)-2-(3-((6-chlorobenzo[d]thiazol-2-yl)(methyl)amino)-6-fluoro-3,4-dihydro-1H-carbazol-9(2H)-yl) acetic acid;
(3S)-2-(3-((5-chlorobenzo[d]thiazol-2-yl)(methyl)amino)-6-fluoro-3,4-dihydro-1H-carbazol-9(2H)-yl) acetic acid;
(3S)-2-(3-((5-chloropyrimidin-2-yl)(2-methoxyethyl)amino)-6-fluoro-3,4-dihydro-1H-carbazol-9(2H)-yl) acetic acid;
(3S)-2-(6-fluoro-3-(methyl(5-(trifluoromethyl)pyridin-2-yl)amino)-3,4-dihydro-1H-carbazol-9(2H)-yl)acetic acid;
(3S)-2-(6-fluoro-3-((5-fluoropyridin-2-yl)(methyl)amino)-3,4-dihydro-1H-carbazol-9(2H)-yl)acetic acid;
(3S)-2-(3-((5-chloropyridin-2-yl)(methyl)amino)-6-fluoro-3,4-dihydro-1H-carbazol-9(2H)-yl)acetic acid;
(3S)-2-(6-fluoro-3-((6-fluorobenzo[d]thiazol-2-yl)(methyl)amino)-3,4-dihydro-1H-carbazol-9(2H)-yl)acetic acid;
(3S)-2-(6-fluoro-3-((5-fluorobenzo[d]thiazol-2-yl)(methyl)amino)-3,4-dihydro-1H-carbazol-9(2H)-yl)acetic acid;
(3S)-2-(6-fluoro-3-((6-chlorobenzo[d]oxazol-2-yl)(methyl)amino)-3,4-dihydro-1H-carbazol-9(2H)-yl)acetic acid; or
(3S)-2-(3-((5-chloropyrimidin-2-yl)(2,2-difluoroethyl)amino)-6-fluoro-3,4-dihydro-1H-carbazol-9(2H)-yl) acetic acid;
or a salt of such a compound.

10. The compound according to claim 1, comprising:
(3S)-2-(3-((5-cyclopropylpyrimidin-2-yl)(methyl)amino)-6-fluoro-3,4-dihydro-1H-carbazol-9(2H)-yl) acetic acid;
(3S)-2-(6-fluoro-3-((6-fluorobenzo[d]oxazol-2-yl)(methyl)amino)-3,4-dihydro-1H-carbazol-9(2H)-yl)acetic acid;
(3S)-2-(6-fluoro-3-(methyl(quinoxalin-2-yl)amino)-3,4-dihydro-1H-carbazol-9(2H)-yl)acetic acid;
2-(6-fluoro-3-(methyl(4-methylthiazol-2-yl)amino)-3,4-dihydro-1H-carbazol-9(2H)-yl)acetic acid;
2-(3-((4-(tert-butyl)thiazol-2-yl)(methyl)amino)-6-fluoro-3,4-dihydro-1H-carbazol-9(2H)-yl)acetic acid;
2-(6-fluoro-3-(methyl(4-(trifluoromethyl)thiazol-2-yl)amino)-3,4-dihydro-1H-carbazol-9(2H)-yl)acetic acid;
2-(3-((5-(tert-butyl)isoxazol-3-yl)(methyl)amino)-6-fluoro-3,4-dihydro-1H-carbazol-9(2H)-yl)acetic acid;
2-(6-fluoro-3-(methyl(1-methyl-1H-pyrazol-3-yl)amino)-3,4-dihydro-1H-carbazol-9(2H)-yl)acetic acid;
2-(6-fluoro-3-(methyl(5-methyl-1,3,4-thiadiazol-2-yl)amino)-3,4-dihydro-1H-carbazol-9(2H)-yl)acetic acid;
2-(6-fluoro-3-(isoxazol-3-yl(methyl)amino)-3,4-dihydro-1H-carbazol-9(2H)-yl)acetic acid;
2-(6-fluoro-3-(methyl(5-methylisoxazol-3-yl)amino)-3,4-dihydro-1H-carbazol-9(2H)-yl)acetic acid;
2-(3((5-chloropyrimidin-2-yl)(methyl)amino)-3,4-dihydro-1H-carbazol-9(2H)-yl)acetic acid;
2-(6-chloro-3-((5-chloropyrimidin-2-yl)(methyl)amino)-3,4-dihydro-1H-carbazol-9(2H)-yl)acetic acid;
2-(3-((5-chloropyrimidin-2-yl)(methyl)amino)-6-methyl-3,4-dihydro-1H-carbazol-9(2H)-yl)acetic acid;
2-(3-((5-chloropyrimidin-2-yl)(methyl)amino)-6-(trifluoromethoxy)-3,4-dihydro-1H-carbazol-9(2H)-yl)acetic acid;
2-(3-((5-chloropyrimidin-2-yl)(methyl)amino)-6-methoxy-3,4-dihydro-1H-carbazol-9(2H)-yl)acetic acid; and
2-(3-((5-chloropyrimidin-2-yl)(methyl)amino)-6-(trifluoromethyl)-3,4-dihydro-1H-carbazol-9(2H)-yl)acetic acid;
or a salt of such a compound.

11. A pharmaceutical composition comprising a compound according to claim 1, or a pharmaceutically acceptable salt thereof, and a pharmaceutically acceptable carrier.

12. A medicinal compound according to claim 1, or a pharmaceutically acceptable salt thereof.

13. A method of preventing and/or treating a disease comprising administering a compound according to claim 1, or a pharmaceutically acceptable salt thereof, wherein the disease is chronic and acute allergic/immune diseases/disorders, basophil-related diseases, or any combination thereof.

14. A method of preventing and/or treating a disease comprising administering a composition according to claim 11, wherein the disease is chronic and acute allergic/immune diseases/disorders, eosinophil-related diseases, basophil-related diseases, or any combination thereof.

15. The method of claim 13, wherein the chronic and acute allergic/immune diseases/disorders is asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, systemic mast cell disorders, anaphylactic shock, urticaria, eczema, ulcerative colitis, chronic obstructive pulmonary disease (COPD), inflammatory bowel disease, rheumatoid arthritis, or any combination thereof.

16. The method of claim 13, wherein eosinophil-related diseases is small vessel vasculitides Churg-Strauss syndrome, Wegener's granulomatosis, microscopic polyangiitis, hypereosinophilic syndromes eosinophilic pneumonia, eosinophilic esophagitis, reflux esophagitis, eosinohilic endocarditis, (Loeffler's endocarditis), eosinophilia-myalgia syndrome, eosinophilic fasciitis, eosinohilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia, DRESS syndrome (Drug Rash with Eosinophilia and Systemic Symptoms), or any combination thereof.

17. The method of claim 13, wherein the basophil-related diseases is basophilic leukemia, basophilic leukocytosis, or a combination thereof.

18. The method of claim 16, wherein the microscopic polyangiitis is organ specific.

19. The compound according to claim 1, wherein the compound is (3S)-2-(6-fluoro-3-((5-chloropyrimidin-2-yl) amino)-3,4-dihydro-1H-carbazol-9-(2H)-yl)acetic acid; or a salt thereof.

20. The compound according to claim 1, wherein the compound is (3S)-2-(6-fluoro-3-((5-fluoropyrimidin-2-yl)(methyl)amino)-3,4-dihydro-1H-carbazol-9(2H)-yl)acetic acid; or a salt thereof.

21. The compound according to claim 1, wherein the compound is (3S)-2-(3-((5-chloropyrimidin-2-yl)(methyl) amino)-6-fluoro-3,4-dihydro-1H-carbazol-9(2H)-yl)acetic acid; or a salt thereof.

22. The compound according to claim 1, wherein the compound is (3S)-2-(3-((5-chlorobenzo [d]oxazol-2-yl)(methyl) amino)-6-fluoro-3,4-dihydro-1H-carbazol-9(2H)-yl)acetic acid; or a salt thereof.

23. The compound according to claim 1, wherein the compound is (3S)-2-(6-fluoro-3-((6-fluorobenzo [d]thiazol-2-yl) (methyl)amino)-3,4-dihydro-1H-carbazol-9(2H)-yl)acetic acid; or a salt thereof.

24. The compound according to claim 1, wherein the compound is (3S)-2-(3-((5-cyclopropylpyrimidin-2-yl)(methyl) amino)-6-fluoro-3,4-dihydro-1H-carbazol-9(2H)-yl)acetic acid; or a salt thereof.

25. The compound according to claim 1, wherein the compound is (3S)-2-(6-fluoro-3-((6-fluorobenzo [d]oxazol-2-yl) (methyl)amino)-3,4-dihydro-1H-carbazol-9(2H)-yl)acetic acid; or a salt thereof.

\* \* \* \* \*

UNITED STATES PATENT AND TRADEMARK OFFICE
CERTIFICATE OF CORRECTION

PATENT NO. : 8,697,869 B2
APPLICATION NO. : 13/637005
DATED : April 15, 2014
INVENTOR(S) : Hamed Aissaoui et al.

It is certified that error appears in the above-identified patent and that said Letters Patent is hereby corrected as shown below:

In the Claims

Column 55, line 49, claim 1, the word "and" should be deleted.

Column 55, lines 62-63, claim 3, should read as follows: "trifluoro-methyl" as opposed to "trifluorom-ethyl".

Column 58, line 37, claim 13, insert --eosinophil-related diseases,-- prior to the phrase "basophil-related diseases".

Signed and Sealed this
Twenty-ninth Day of July, 2014

Michelle K. Lee
*Deputy Director of the United States Patent and Trademark Office*